US008025883B2

(12) United States Patent
Brooks et al.

(10) Patent No.: US 8,025,883 B2
(45) Date of Patent: *Sep. 27, 2011

(54) ANTAGONISTS AND METHODS FOR INHIBITING ANGIOGENESIS

(75) Inventors: Peter C. Brooks, Hollywood, CA (US); Jingsong Xu, Alhambra, CA (US); Eric Petitclerc, Quebec (CA)

(73) Assignee: University of Southern California, Los Angeles, CA (US)

(*) Notice: Subject to any disclaimer, the term of this patent is extended or adjusted under 35 U.S.C. 154(b) by 965 days.

This patent is subject to a terminal disclaimer.

(21) Appl. No.: 11/227,524

(22) Filed: Sep. 15, 2005

(65) Prior Publication Data

US 2006/0088540 A1   Apr. 27, 2006

Related U.S. Application Data

(62) Division of application No. 09/478,977, filed on Jan. 6, 2000, now Pat. No. 7,122,635.

(60) Provisional application No. 60/114,877, filed on Jan. 6, 1999, provisional application No. 60/114,878, filed on Jan. 6, 1999, provisional application No. 60/152,496, filed on Sep. 2, 1999, provisional application No. 60/143,534, filed on Jul. 13, 1999.

(51) Int. Cl.
  *A61K 39/395* (2006.01)
  *C07K 14/705* (2006.01)
  *C07K 16/28* (2006.01)
  *C07K 14/78* (2006.01)
  *C07K 16/30* (2006.01)

(52) U.S. Cl. ............... 424/155.1; 424/130.1; 424/134.1; 424/135.1; 424/152.1; 424/153.1; 424/154.1; 424/172.1; 424/173.1; 424/174.1

(58) Field of Classification Search ............... 424/130.1, 424/134.1, 135.1, 136.1, 152.1, 153.1, 154.1, 424/155.1, 172.1, 173.1, 174.1
See application file for complete search history.

(56) References Cited

U.S. PATENT DOCUMENTS

| 5,320,970 | A | 6/1994 | Eyre |
| 5,530,101 | A | 6/1996 | Queen et al. ............... 530/387.3 |
| 5,541,295 | A | 7/1996 | Barrach et al. ............. 530/388.1 |
| 5,693,762 | A | 12/1997 | Queen et al. |
| 5,763,272 | A | 6/1998 | Naser et al. .................... 435/325 |
| 5,972,623 | A | 10/1999 | Krane et al. ................... 435/7.1 |
| 6,030,792 | A | 2/2000 | Otterness et al. ............. 435/7.1 |
| 6,132,976 | A | 10/2000 | Poole et al. .................... 435/7.1 |
| 6,521,593 | B1 * | 2/2003 | Laug ................................. 514/9 |
| 6,833,373 | B1 * | 12/2004 | McKearn et al. ............. 514/272 |

FOREIGN PATENT DOCUMENTS

| EP | 0 510 949 A2 | 10/1992 |
| EP | 0 921395 | 6/1999 |
| EP | 0992586 | 4/2000 |
| WO | WO9414070 | 6/1994 |
| WO | WO9504282 | 2/1995 |
| WO | WO9744059 | 11/1997 |
| WO | WO9835235 | 8/1998 |
| WO | WO9906840 | 2/1999 |

OTHER PUBLICATIONS

Davis, G.E. et al., Biochemical and Biophysical Research Communications, 182(3): 1025-1031, 1992.*
Heino, J., BioEssays 29: 1001-1010, 2007.*
Ingham, K.C., et al. Archives of Biochemistry and Biophysics, 407: 217-223, 2002.*
Timpl, R., "Antibodies to Collagens and Precollagens", Mtehods in Enzymology, 82 Pt A:472-498 (1982).
Jellinek, et al., "Inhibition of Receptor Binding by High-Affinity RNA Ligands to Vascular Endothelial Growth Factor", Biochemistry, 33 (34):10450-10456 (1994).
Tuerk, C., et al., "Systematic Evolution of Ligands by Exponential Enrichment", RNA Ligands to Bacteriophage T4 DNA Polymerase, Science 249, (Aug. 3, 1990) pp. 505-510.
Ecker, D., et al., Rational Screening of Oligonucleotide Combinatorial Libraries for Drug Discovery, Nucleic Acids Research, vol. 21, No. 8, pp. 1853-1856, (1993).
Wick, G., et al., "Characterization of Antibodies to Basement Membrane (Type IV) Collagen in Immunohistological Studies", Immunobiology, vol. 156, pp. 371-381 (1979).
Bellon, G, "Quantification and Specific Detection of Collagenous Proteins Using an Enzyme-Linked Immunosorbent Assay and an Immunoblotting for Cyanogen Bromide Peptides", Analytical Biochemistry, 1985, vol. 150, pp. 188-202.
Brooks, et al., "Antiintegrin αv83 Blocks Human Breast Cancer Growth and Angiogenesis in Human Skin", J. Clin. Invest. Oct. 1995, vol. 96, pp. 1815-1822.
Petitclerc, et al., "Integrin Alpha V Beta 3 Promotes M21 Melanoma Growth in Human Skin by Regulating Tumor Cell Survival", Cancer Research 59:2724-2730, Jun. 1, 1999. Borza, Donn-Bogdan, et al., "*Identification of Multiple Cryptic Epitopes on the NC1 Domain of the a3(IV) Collagen Chain*," The Journal of Biological Chemistry, vol. 275, No. 8, Feb. 25, 2000, pp. 6030-6037.
David, Michelle, et al., "*Hydrophobic Amino Acid Residues Are Critical for the Immunodominant Epitope of the Goodpasture Autoantigen*," The Journal of Biological Chemistry, vol. 276, No. 9, 2001, pp. 6370-6377.
Greenspan, Neil S., et al., "*Defining Epitopes: It's Not As Easy As It Seems*," Nature Biotechnology, vol. 17, Oct. 1999, pp. 936-937.
Kalluri, Raghu, et al. "*Specificity of Circulating and Tissue-Bound Autoantibodies in Goodpasture Syndrome*," Proceedings of the Association of American Physicians, 1996, pp. 135-139.

(Continued)

Primary Examiner — Alana M Harris
Assistant Examiner — Anne Holleran
(74) Attorney, Agent, or Firm — DLA Piper LLP (US)

(57) ABSTRACT

The invention describes methods for inhibiting angiogenesis in a tissue by administering an antagonist that specifically binds to a proteolyzed or denatured collagen but not to native triple helical forms of the collagen. Antagonists of the invention can target, for example, denatured collagens type-I, type-II, type-III, type-IV, type-V and combinations thereof. Methods utilizing such antagonists for therapeutic treatment of tumor growth, tumor metastasis or of restenosis also are described, as are methods to use such antagonists as diagnostic markers of angiogenesis is normal or diseased tissues both in vivo and ex vivo. Antagonists include monoclonal antibodies referred to as HUI77, HUIV26, and XL313.

12 Claims, 33 Drawing Sheets

OTHER PUBLICATIONS

Mariuzza, R.A., et al. "*The Structural Basis of Antigen-Antibody Recognition*," Am. Rev. Biophys., Biophys. Chem. 1987, pp. 139-159.

Nakanishi, Koichi, et al., "*Immunohistochemical Study of α1-5 Chains of Type IV Collagen in Hereditary Nephritis*," Kidney International, vol. 46, 1994, pp. 1413-1421.

Wheatcroft, A.C., "*Evidence of In Situ Stability of the Type IV Collagen Triple Helix in Human Inflammatory Bowel Disease Using a Denaturation Specific Epitope Antibody*," Matrix Biology 18, 1999, pp. 361-372.

Yang, Wei-Ping, et al., "*CDR Walking Mutagenesis for the Affinity Maturation of a Potent Human Anti-HIV-1 Antibody into the Picomolar Range*," J. Mol. Biol., 1995, 254, pp. 392-403.

Yoshioka, Kazuo, et al., "*Normal Distribution and Abnormalities in X-Linked Alport Syndrome Revealed by Monoclonal Antibody*," American Journal of Pathology, vol. 144, No. 5, 1994, pp. 986-996.

Xu, Jingson, et al., "*Generation of Monoclonal Antibodies to Cryptic Collagen Sites by Using Subtractive Immunization*," Hybridoma, vol. 19, Nov. 5, 2000, pp. 375-385.

\* cited by examiner

Figure 3
Human Melanoma
(Biopsy)
Human Melanoma
(Human / SCID Mouse Chimera)
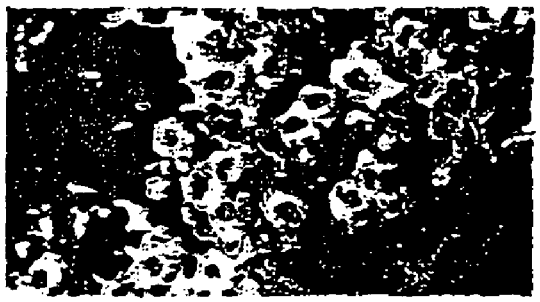
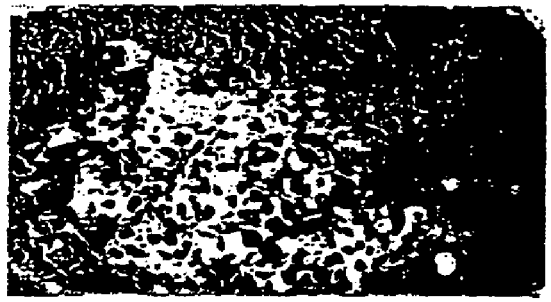

Figure 4
Human Melanoma Biopsy
Anti-Factor VIII
(Polyclonal Ab)
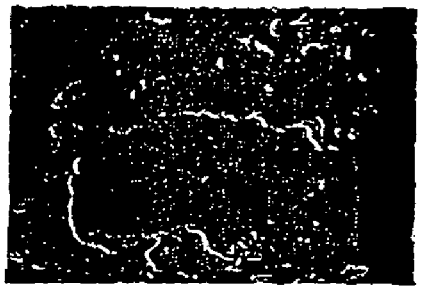
Anti-Denatured Collagen
(Monoclonal Ab HU177)

Chick CAM Angiogenesis Assay

CS-1 Melanoma Tumor Assay

Figure 11
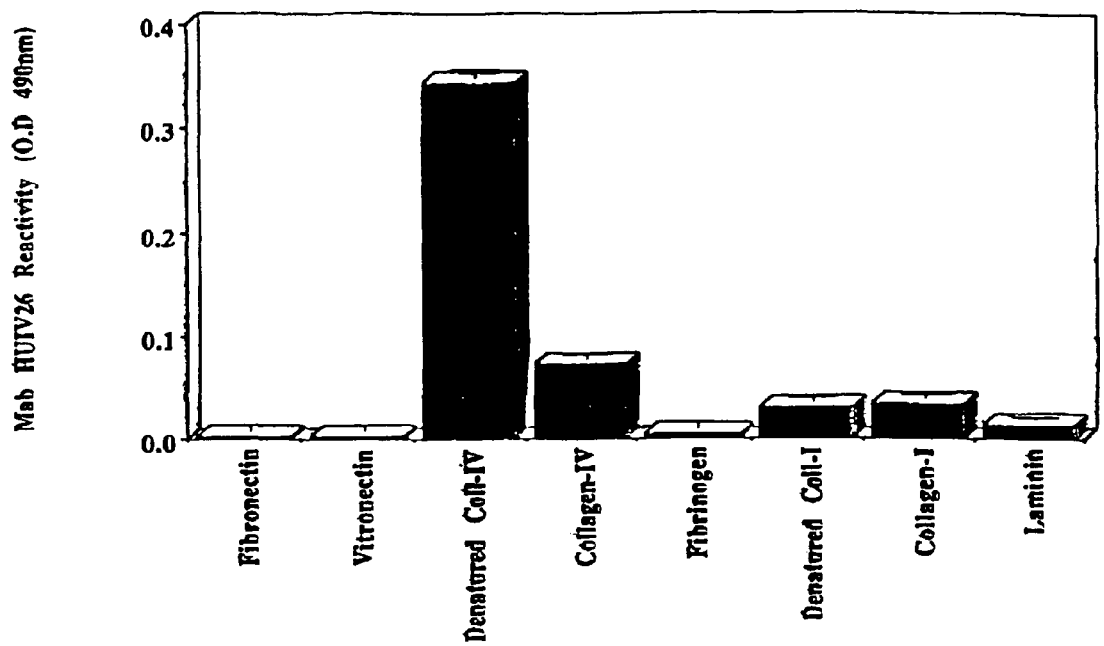
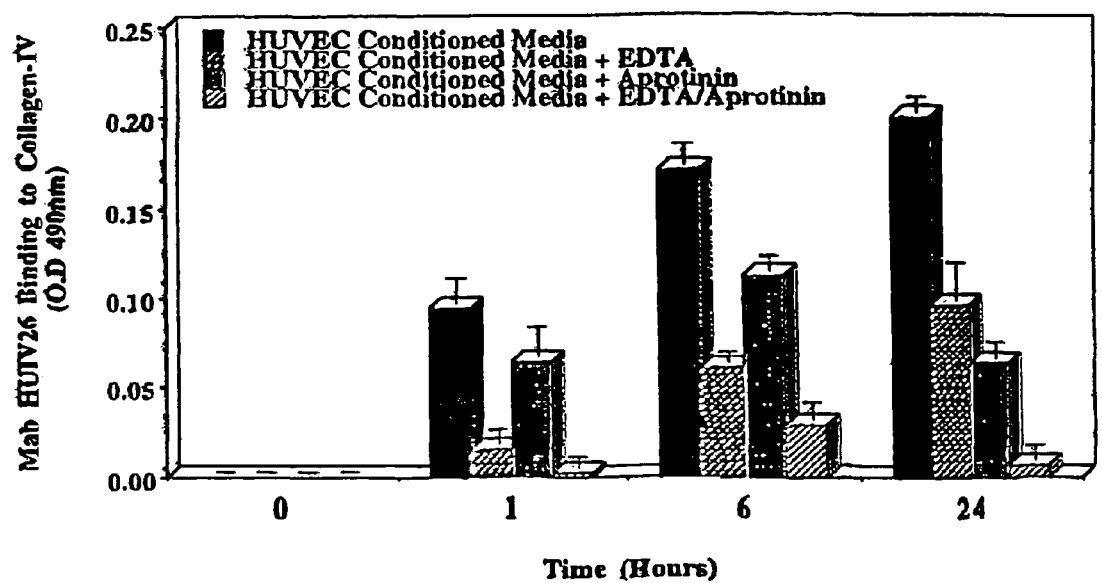

Figure 13
Human Melanoma Tumor Biopsy
Anti-Factor VIII
(Polyclonal Ab)
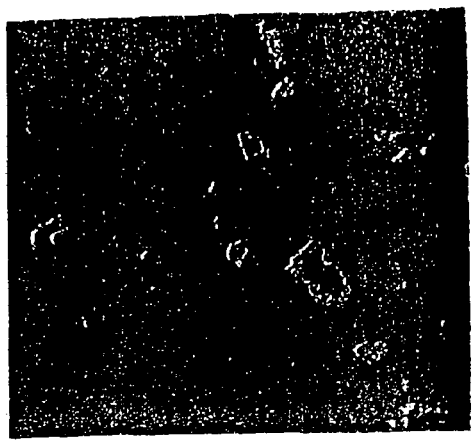
Anti-Denatured Coll-IV
(Mab HUIV26)
Co-Staining of Human Melanoma Biopsy
(Anti-Factor VIII / Anti-Denatured Coll-IV)

Figure 16
N0 bFGF  
bFGF  
bFGF + HUIV26 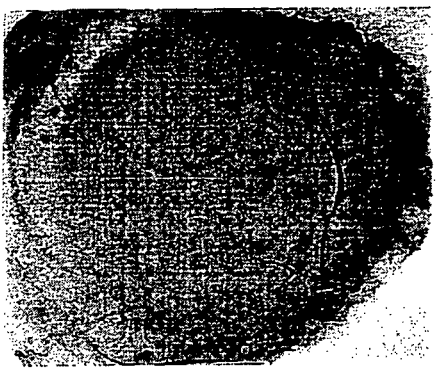 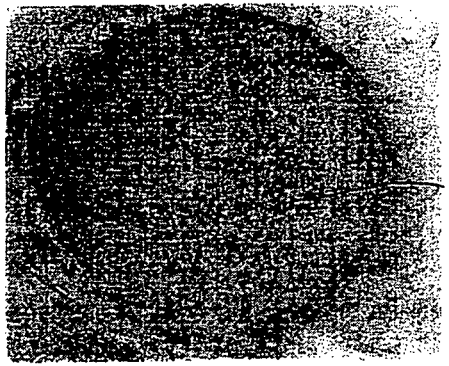
bFGF + Control 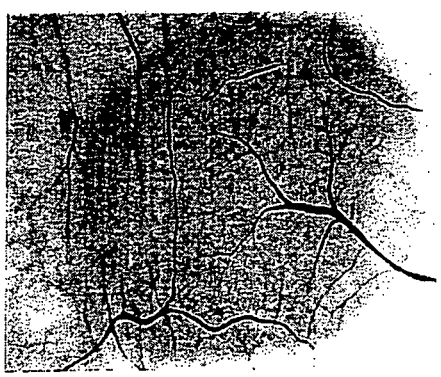 

Figure 18
CS-1 Melanoma Tumor Growth In The Chick CAM
Control Mab
 
HUIV26 Mab
 

Figure 22
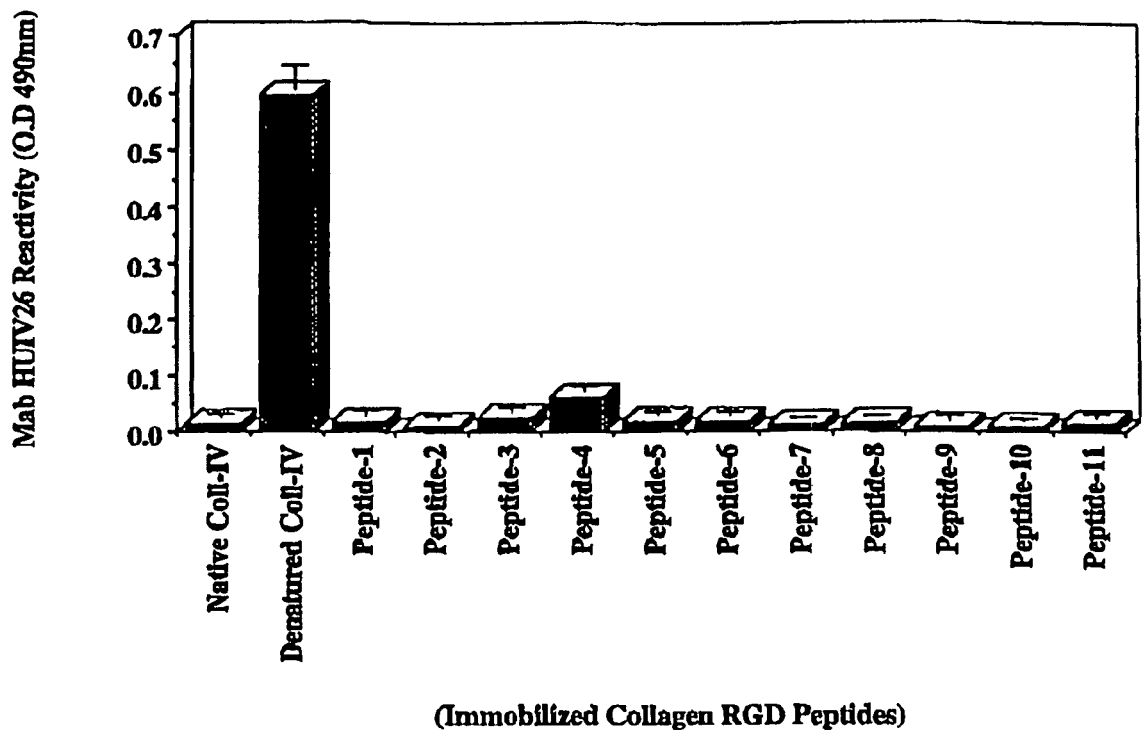
(Immobilized Collagen RGD Peptides)
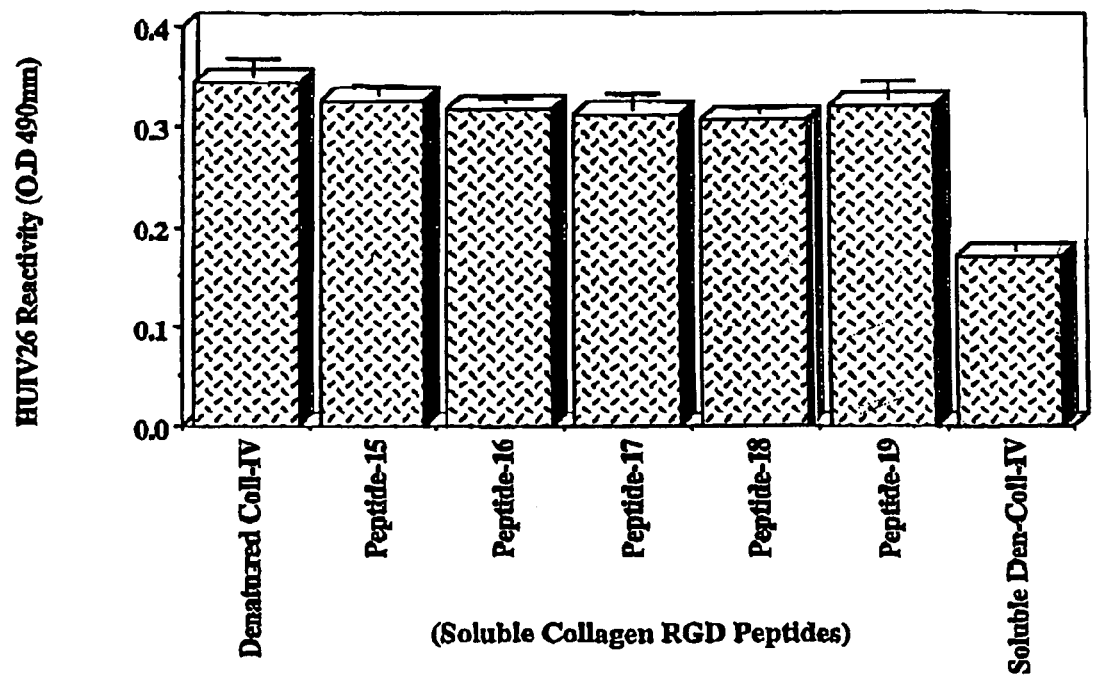
(Soluble Collagen RGD Peptides)

Figure 23
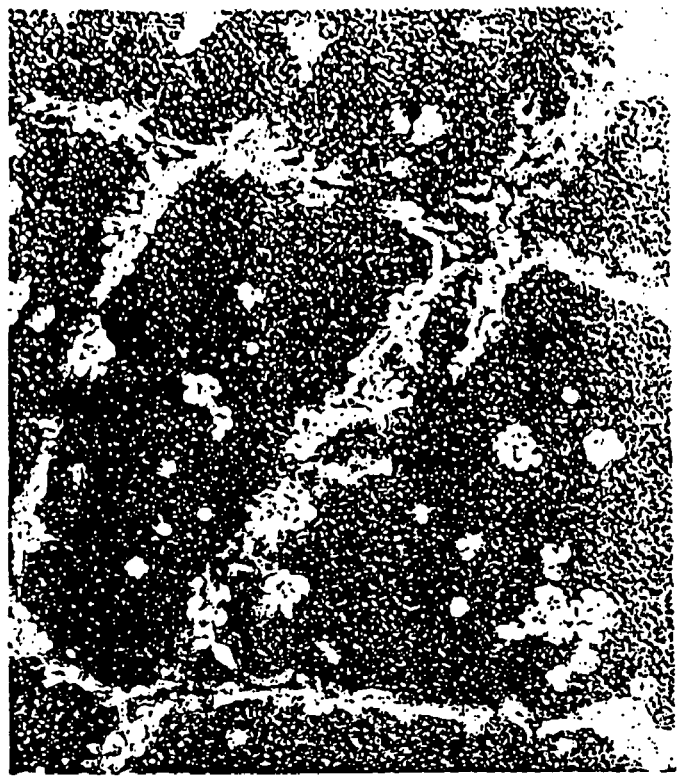
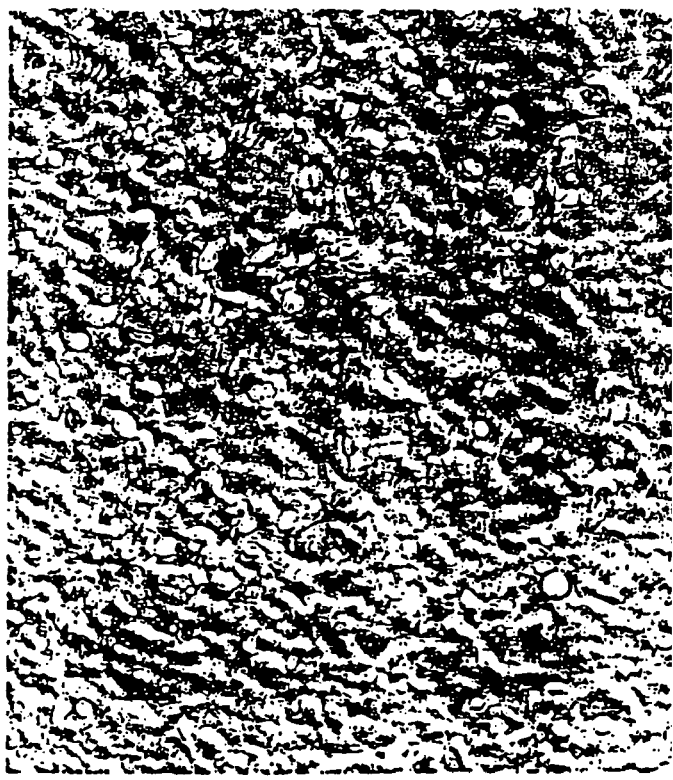

Effects of Cryptic Collagen Domains on Endothelial Cord Formation
Flexible millipore membranes were coated with either native collagen-I (Coll-I) or collagen Peptides 1 through 5. Human endothelial cells were allowed to attach to the coated membranes for either 1 or 18 hours. Representative photographs of cord formation.

A.
Figure 26
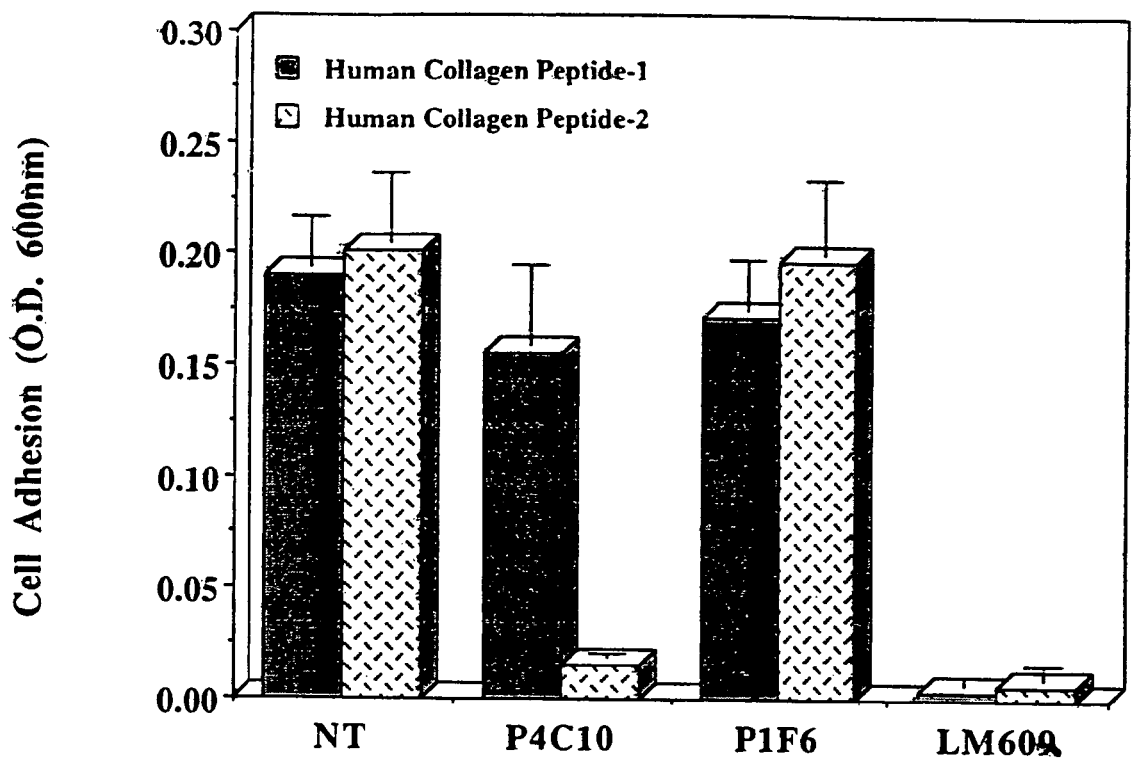
B.
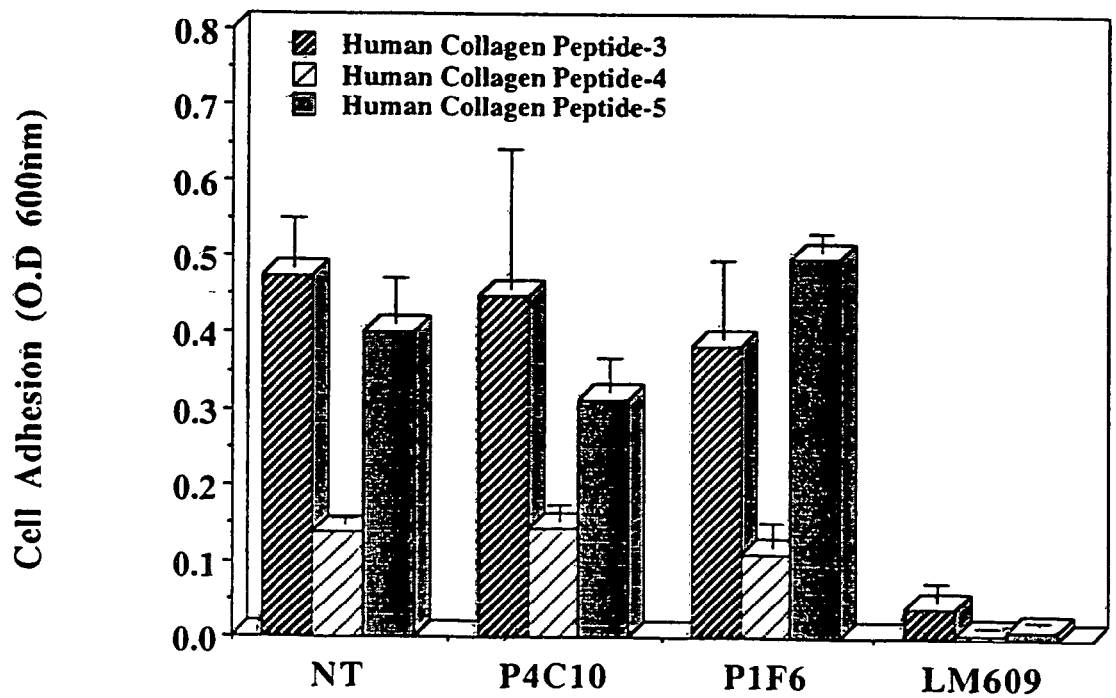

Mab XL313 Reactivity (O.D 490nm)

Figure 29
bFGF Induced Angiogenesis in the Chick CAM
bFGF
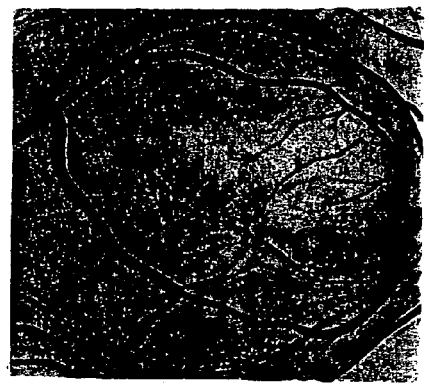
bFGF + Mab XL313
bFGF + Mab Control

Chick CAM Angiogenesis Assay

HT1080 Human Fibrosarcoma Tumor Growth

A.
FIGURE 33
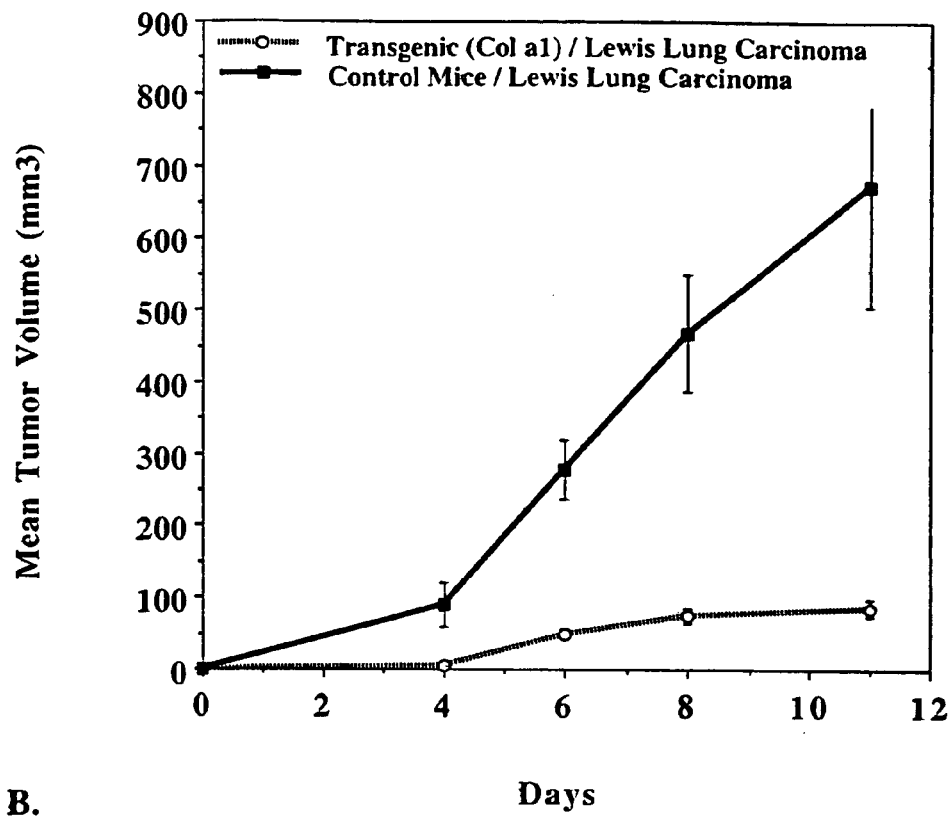
B.
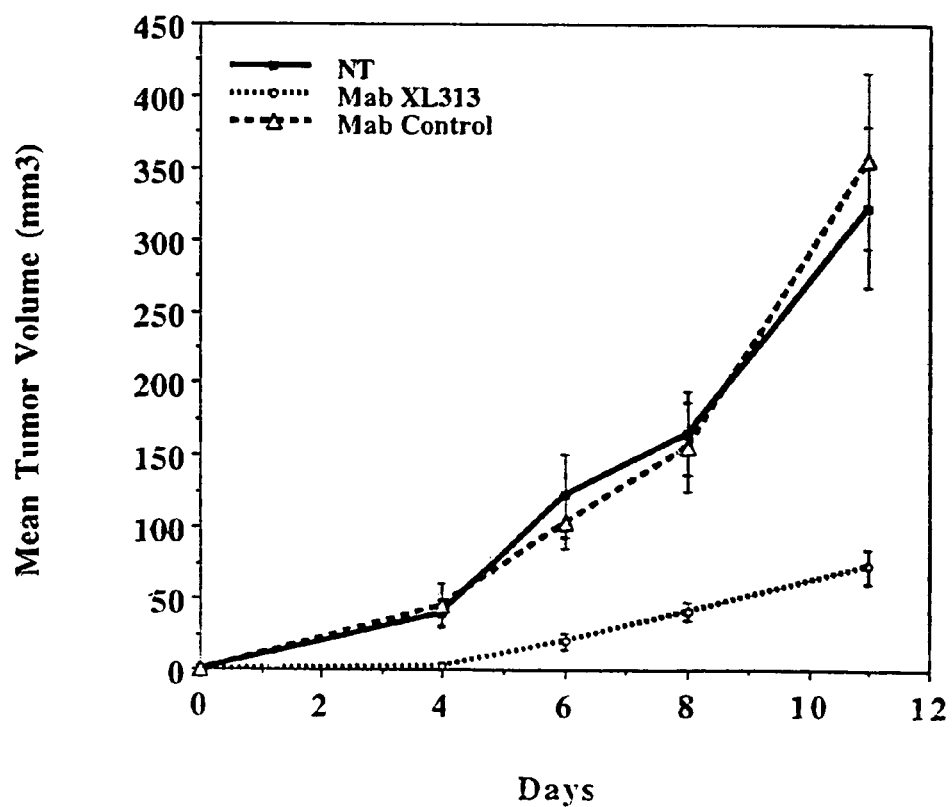

SEQUENCE LISTING

<160> NUMBER OF SEQ ID NOS: 13

<210> SEQ ID NO 1
<211> LENGTH: 11
<212> TYPE: PRT
<213> ORGANISM: Homo sapiens

<400> SEQUENCE: 1

```
Cys Pro Gly Ser Arg Gly Asp Thr Gly Pro Cys
1               5                   10
```

<210> SEQ ID NO 2
<211> LENGTH: 11
<212> TYPE: PRT
<213> ORGANISM: Homo sapiens

<400> SEQUENCE: 2

```
Cys Ser Gly Pro Arg Gly Asp Pro Gly Leu Cys
1               5                   10
```

<210> SEQ ID NO 3
<211> LENGTH: 11
<212> TYPE: PRT
<213> ORGANISM: Homo sapiens

<400> SEQUENCE: 3

```
Cys Lys Gly Ser Arg Gly Asp Pro Gly Thr Cys
1               5                   10
```

<210> SEQ ID NO 4
<211> LENGTH: 11
<212> TYPE: PRT
<213> ORGANISM: Homo sapiens

<400> SEQUENCE: 4

```
Cys Lys Gly Ala Arg Gly Asp Pro Gly Phe Cys
1               5                   10
```

<210> SEQ ID NO 5
<211> LENGTH: 11
<212> TYPE: PRT
<213> ORGANISM: Homo sapiens

<400> SEQUENCE: 5

```
Cys Pro Gly Pro Arg Gly Asp Ala Gly Val Cys
1               5                   10
```

<210> SEQ ID NO 6
<211> LENGTH: 11
<212> TYPE: PRT
<213> ORGANISM: Homo sapiens

<400> SEQUENCE: 6

```
Cys Pro Gly Asp Arg Gly Asp Pro Gly Asp Cys
1               5                   10
```

<210> SEQ ID NO 7
<211> LENGTH: 11
<212> TYPE: PRT
<213> ORGANISM: Homo sapiens

<400> SEQUENCE: 7

```
Cys Ser Gly Asp Arg Gly Asp Ala Gly Phe Cys
1               5                   10
```

<210> SEQ ID NO 8
<211> LENGTH: 11
<212> TYPE: PRT
<213> ORGANISM: Homo sapiens

<400> SEQUENCE: 8

```
Cys Lys Gly Ser Arg Gly Asp Pro Gly Pro Cys
1               5                   10
```

```
<210> SEQ ID NO 9
<211> LENGTH: 11
<212> TYPE: PRT
<213> ORGANISM: Homo sapiens

<400> SEQUENCE: 9

Cys Ile Gly Ser Arg Gly Asp Lys Gly Ala Cys
 1               5                   10

<210> SEQ ID NO 10
<211> LENGTH: 11
<212> TYPE: PRT
<213> ORGANISM: Homo sapiens

<400> SEQUENCE: 10

Cys Pro Gly Glu Arg Gly Asp Pro Gly Glu Cys
 1               5                   10

<210> SEQ ID NO 11
<211> LENGTH: 11
<212> TYPE: PRT
<213> ORGANISM: Homo sapiens

<400> SEQUENCE: 11

Cys Pro Gly Phe Arg Gly Asp Glu Gly Pro Cys
 1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Cys Gln Gly Pro Arg Gly Asp Lys Gly Glu Cys
 1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Cys Gln Gly Pro Arg Gly Asp Ala Ala Ala Cys
 1               5                   10
```

ANTAGONISTS AND METHODS FOR INHIBITING ANGIOGENESIS

RELATED APPLICATION DATA

This application is a divisional of Ser. No. 09/478,977, filed on Jan. 6, 2000, now U.S. Pat. No. 7,122,635 entitled "Methods and Composition for Angiogenesis Inhibition," which claims priority to provisional application Ser. No. 60/114,877 filed Jan. 6, 1999, provisional application Ser. No. 60/114,878 filed Jan. 6, 1999, provisional application Ser. No. 60/152,496 filed Sep. 2, 1999, provisional application Ser. No. 60/143,534 filed Jul. 13, 1999. The entire disclosures of these applications are incorporated herein by reference.

STATEMENT REGARDING FEDERALLY SPONSORED RESEARCH OR DEVELOPMENT

This invention was made with government support under Contract No. CA074132 awarded by the National Institutes of Health. The government has certain rights in the invention.

FIELD OF INVENTION

The invention relates generally to the field of medicine, and relates specifically to methods and compositions for inhibiting angiogenesis in a tissue or detecting angiogenesis using antagonists of denatured or proteolyzed forms of collagen including, but not limited to types I, II, III, IV and V.

BACKGROUND

Tumor growth and metastasis impacts a large number of people each year. In fact, it is estimated that well over 600,000 new cases of cancer will be diagnosed in the coming year in the United States alone (Varner, J. A., Brooks, P. C., and Cheresh, D. A. (1995) *Cell Adh. Commun.* 3, 367-374). Importantly, numerous studies have suggested that the growth of all solid tumors requires new blood vessel growth for continued expansion of the tumors beyond a minimal size (Varner et al. 1995; Blood, C. H. and Zetter, B. R. (1990) *Biochim. Biophys. Acta.* 1032:89-118; Weidner, N. et al. (1992) *J. Natl. Cancer Inst.* 84:1875-1887; Weidner, N. et al. (1991). *N. Engl. J. Med.* 324:1-7; Brooks, P. C. et al. (1995) *J. Clin. Invest.* 96:1815-1822; Brooks, P. C. et al. (1994) *Cell* 79:1157-1164; Brooks, P. C. et al (1996). *Cell* 85, 683-693; Brooks, P. C. et al. (1998) *Cell* 92:391-400. Significantly, a wide variety of other human diseases also are characterized by unregulated blood vessel development, including ocular diseases such as macular degeneration and diabetic retinopathy. In addition, numerous inflammatory diseases also are associated with uncontrolled neovascularization such as arthritis and psoriasis (Varner et al. 1995). Angiogenesis is the physiological process by which new blood vessels develop from pre-existing vessels (Varner et al. 1995; Blood and Zetter 1990; Weidner et al. 1992). This complex process requires cooperation of a variety of molecules including growth factors, cell adhesion receptors, matrix degrading enzymes and extracellular matrix components (Varner et al. 1995; Blood and Zetter 1990; Weidner et al. 1992). Thus, therapies designed to block angiogenesis may significantly effect the growth of solid tumors. In fact, clear evidence has been provided that blocking tumor neovascularization can significantly inhibit tumor growth in various animal models, and human clinical data is beginning to support this contention as well (Varner, J. A., Brooks, P. C., and Cheresh, D. A. (1995) *Cell Adh. Commun.* 3, 367-374). Importantly, numerous studies have suggested that the growth of all solid tumors requires new blood vessel growth for continued expansion of the tumors beyond a minimal size (Varner et al. 1995; Blood and Zetter 1990; Weidner et al. 1992; Weidner et al. 1991; Brooks et al. 1995; Brooks et al. 1994; Brooks et al. 1997).

To this end, many investigators have focused their anti-angiogenic approaches towards growth factors and cytokines that initiate angiogenesis (Varner et al. 1995; Blood and Zener 1990; Weidner et al. 1992; Weidner et al. 1991; Brooks et al. 1995; Brooks et al. 1994; Brooks et al. 1997). However, there is a large number of distinct growth factors and cytokines which have the capacity to stimulate angiogenesis. The therapeutic benefit of blocking a single cytokine may have only limited benefit due to this redundancy. However, little attention has been directed to other anti-angiogenic tar-gets. Recent studies have suggested that angiogenesis requires proteolytic remodeling of the extracellular matrix (ECM) surrounding blood vessels in order to provide a microenvironment conducive to new blood vessel development (Varner et al. 1995; Blood and Zetter 1990; Weidner et al. 1992; Weidner et al. 1991; Brooks et al. 1995; Brooks et al. 1994; Brooks et al. 1997). The extracellular matrix protein collagen makes up over 25% of the total protein mass in animals and the majority of protein within the ECM. Collagen is a fibrous multi-chain triple helical protein that exists in numerous forms (Olsen, B. R. (1995) *Curr. Opin. Cell Biol.* 7, 720-727; Van der Rest, M., and Garrone, R. (1991) *FASEB* 5, 2814-2823). At least 18 genetically distinct types of collagen have been identified, many of which have distinct tissue distributions and functions (Olsen 1995; Van der Rest and Garrone 1991). Collagen type-I is the most abundant collagen type in the extracellular matrix. Collagen type-I, type-III, collagen type-IV and collagen type-V have been shown to be associated with all pre-existing blood vessels in vivo. Collagens type-I and type-IV are composed of major chains designated $\alpha 1(I)$ and $\alpha 2(I)$ and $\alpha 1(IV)$ and $\alpha 2(IV)$ respectively. The mature collagen molecule is composed of two $\alpha 1$ chains and one $\alpha 2$ chain twisted into a triple helix. In vivo, collagen is normally found in the mature triple helical form. Denaturation of the native three dimensional structure of mature triple helical collagen may expose cryptic regulatory regions that control angiogenesis. Antagonism of these cryptic regulatory regions could provide an unrecognized means for the diagnosis and inhibition of angiogenesis.

It has been proposed that inhibition of angiogenesis would be a useful therapy for restricting tumor growth. Inhibition of angiogenesis has been proposed by (1) inhibition of release of "angiogenic molecules" such as βFGF (fibroblast growth factor), (2) neutralization of angiogenic molecules, such as by use of anti-βFGF antibodies, and (3) inhibition of endothelial cell response to angiogenic stimuli. This latter strategy has received attention, and Folkman et al., Cancer Biology, 3:89-96 (1992), have described several endothelial cell response inhibitors, including collagenase inhibitors, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like that might be used to inhibit angiogenesis. For additional proposed inhibitors of angiogenesis, see Blood and Zetter 1990; Moses et al. (1990) *Science* 248:1408-1410; Ingber et al. (1988) *Lab. Invest.*, 59:44-51; and U.S. Pat. Nos. 5,092,885, 5,112,946, 5,192,744, and 5,202,352. None of the inhibitors of angiogenesis described in the foregoing references target denatured or proteolyzed collagens.

SUMMARY

The present invention provides antagonists of denatured or proteolyzed collagens that can inhibit angiogenesis. Antagonists specifically bind to a denatured or proteolyzed collagen, but bind with substantially reduced affinity to native forms of the same collagen. Antagonists can be specific for any denatured collagen, including denatured collagen type-I, denatured collagen type-II, denatured collagen type-III, denatured collagen type-IV or denatured collagen type-V, or for combinations thereof. For example, in one embodiment, an antagonist is specific for denatured collagen type-I relative to native triple helical collagen type-I but binds with substantially reduced affinity to other denatured collagens, such as collagen type-IV. In another embodiment, an antagonist is specific for denatured collagen type-IV. An antagonist can also be specific for denatured collagen types I, II, III, IV and V.

An antagonist can be an antibody or functional fragment thereof, that immunoreacts with denatured collagen but immunoreacts to a substantially lesser extent with the native form of the collagen. Antibodies can be monoclonal or polyclonal. An antagonist also can be a polypeptide or peptide with specificity for a denatured collagen, but not for a native form of the collagen. Antagonists also can be non-peptidic compounds such as a small organic molecule or an oligonucleotides.

The invention therefore describes methods for inhibiting angiogenesis in a tissue comprising administering to the tissue a composition comprising an angiogenesis-inhibiting amount of an antagonist of denatured/proteolyzed collagen.

The tissue to be treated can be any tissue in which inhibition of angiogenesis is desirable, such as diseased tissue where neo-vascularization is occurring. Exemplary tissues include inflamed tissue, solid tumors, metastases, tissues undergoing restenosis, and the like.

The invention also provides methods for detecting angiogenesis in a tissue by contacting an antagonist of the invention with the tissue. Such methods are appropriate for use both ex vivo and in vivo.

Methods also are provided for detecting tumorous tissue, metastases, and tumor invasion into a tissue by contacting an antagonist of the invention with a tissue either ex vivo or in vivo.

The invention also provides methods for screening antagonists that bind specifically to a denatured collagen or collagens, but bind with substantially reduced affinity to the native form of the collagen or collagens and can inhibit angiogenesis.

BRIEF DESCRIPTION OF THE FIGURES

FIG. 3 shows that Mab HUI77 identifies denatured collagen surrounding human melanoma tumors in vivo. The generation and localization of denatured collagen in vivo was studied by indirect immunofluoresence on frozen tissue sections of human melanomas from both the human mouse chimeric model and human tumor biopsies. Frozen tissue sections from human melanomas were fixed in acetone, blocked with 1% BSA and co-stained with Mab HUI77 and polyclonal antibody directed to $\alpha_v$ integrin expressed on the human melanoma cells. Antibody binding was detected by incubation with goat-anti-mouse FITC conjugated and goat anti-rabbit rhodamine conjugated secondary antibody. Left panels indicate human melanoma tumor biopsy (630X). Right panels indicate M21 human melanoma cell line grown within full thickness human skin (200X). Red indicates $\alpha_v$ integrin expression and green indicates denatured collagen expression. Yellow indicates co-localization of $\alpha_v$ integrins and denatured collagen.

FIG. 4 shows that Mab HUI77 identifies denatured collagen surrounding human melanoma tumor associated blood vessels. The generation and localization of denatured collagen in vivo was studied by indirect immunofluoresence on frozen tissue sections of human melanoma tumor biopsies. Frozen tissue sections from human melanomas were fixed in acetone, blocked with 1% BSA and co-stained with Mab HUI77 and polyclonal antibody directed to factor VIII, a known marker of blood vessels. Antibody binding was detected by incubation with goat-anti-mouse fluorescein isothiocyanate (FITC) conjugated and goat anti-rabbit rhodamine conjugated secondary antibodies. Left panel shows human melanoma tumor biopsy staining for factor VIII (Red) outlining a tumor blood vessel. Right panel shows denatured collagen (Green) surrounding the human tumor associated blood vessel.

FIG. 11 demonstrates Mab HUIV26 reactivity with extacellular matrix components in solid phase ELISA. Microtiter plates were coated with extracellular matrix components, each at a concentration of 25 ug/ml. A). Mab HUIV26 was added at a concentration of 1 ug/ml, followed 1 hour later with goat anti-mouse peroxidase labeled IgG. Denatured collagen type-I and collagen type-IV were prepared by boiling for 15 minutes before coating the plates. All data were corrected for any non-specific binding of secondary antibody. Data bars represent the mean optical density (O.D.)±standard deviations from triplicate wells. B). Microtiter wells were coated with triple helical collagen type-IV at 25 ug/ml. Concentrated (20x) HUVEC conditioned media was added to the wells in the presence or absence of EDTA, Aprotinin or both and allowed to incubate for 1, 6 and 24 hours. The plates were next washed, blocked and incubated with Mab HUIV26 or control antibody. All data were corrected for non-specific secondary antibody binding. Data bars represent the mean optical density (O.D.)±standard deviations from triplicate wells. The following abbreviations are used in the figure Coll-I, collagen type-I; Coll-IV, collagen type-IV.

FIG. 13 shows that Mab HUIV26 identifies denatured collagen type-IV surrounding human melanoma tumor associated blood vessels. The generation and localization of denatured collagen-IV in vivo was studied by indirect immunofluoresence on frozen tissue sections of human melanomas tumor biopsies. Frozen tissue sections from human melanomas were fixed in acetone, blocked with 1% BSA and co-stained with Mab HUIV26 and polyclonal antibody directed to factor VIII a known marker of blood vessels. Antibody binding was detected by incubation with goat-anti-mouse FITC conjugated and goat anti-rabbit rhodamine conjugated secondary antibody. Red indicates factor VIII expression and marks the human blood vessels. Green indicates denatured collagen-IV specifically associated with the tumor associated angiogenic blood vessels.

FIG. 16 demonstrates the effects of systemic administration of purified Mab HUIV26 on angiogenesis in vivo. Filter discs saturated with bFGF were place on the Chorioallantoic Membranes (CAMs) of 10 day old chick embryos. Twenty four hours latter the embryos received a single intravenous injection with 20 ug of Mab HUIV26 or a control. At the end of a 3 day incubation period the filter discs and surrounding CAM tissues were removed and angiogenesis was quantified by counting the number of blood vessel branch points with the area of the filter disc. FIG. 6 shows examples of CAM tissue from a typical experiment.

FIG. 18 shows the effects of systemic administration of purified Mab HUIV26 on tumor growth in vivo. CS-1 melanoma tumor cells ($5 \times 10^6$) were inoculated on the CAMs of 10 day old chick embryos. Twenty four hours latter the embryos received a single intravenous injection of 20 μg of purified Mab HUIV26 or control. The embryos were allowed to incubate for a total of 7 days. Photographs represent examples of tumors from control or HUIV26 treated embryos within the CAM tissue.

FIG. 22 shows an analysis of Mab HUIV26 reactivity with RGD containing collagen peptides. Microtiter plates were coated with 50 ul of either RGD containing collagen peptides (100 ug/ml) (A) or denatured human collagen type-IV (B). Plates were blocked with 1% BSA in PBS to prevent non-specific binding. Mab HUIV26 (1.0 ug/ml, 50 ul/well) was allowed to bind to the coated plate for 1 hour at 37° C. Mab HUIV26 binding was detected by incubation with peroxidase labeled secondary antibody. Immunoreactivity was quantified by measuring optical density (O.D.) with a microtiter plate reader. A). Immunoreactivity of purified Mab HUIV26 to RGD containing collagen peptides. B). Immunoreactivity of HUIV26 binding to immobilized denatured collagen type-IV in the presence or absence of soluble RGD containing collagen peptides or denatured collagen type-IV. Data bars represent the mean O.D.±standard deviation from triplicate wells.

FIG. 23 shows human endothelial cord formation on denatured Collagen type-I. Flexible Millipore membranes were coated with either native or denatured human collagen type-I. Human endothelial cells (HUVECs) were allowed to interact with the collagen for 5 hours in the absence of added growth factors or serum.

FIG. 26 shows that cryptic domains of collagen type-I support endothelial cell adhesion by distinct integrin receptors. Peptides representing cryptic domains of human collagen-I were immobilized on microtiter wells. Endothelial cells were allowed to attach to the peptides in the presence or absence of function blocking antibodies directed to specific integrins. All peptides supported cell adhesion to varying levels. Cell adhesion to all 5 peptides were dependent on ligation of integrin αvβ3 since Mab LM609 directed to αvβ3 blocked cell adhesion. Surprisingly, cell adhesion to peptide-2 was also dependent on a β1 integrin, since cell adhesion to this peptide was also blocked by P4C10 directed to β1 integrins.

FIG. 29 shows that Mab XL313 inhibits angiogenesis in the chick. Angiogenesis was induced on the CAMs of 10 day old chick embryos with bFGF. Twenty-four hours later the embryos received a single IV injection with 50 μg of Mab XL313 or an isotype matched control. Three days later, angiogenesis was quantified by counting the number of blood vessel branch points within the area of the filter disc. A; Representative examples of CAM tissue from a typical experiment.

FIG. 33 shows that Mab XL313 inhibits tumor growth in B6 mice. The growth of Lewis lung carcinoma tumors were examined in either wild type B6 mice or Col a1 transgenic mice. A; Lewis lung carcinoma cells were injected subcutaneously into either wild-type B6 mice or B6 col a1 transgenic mice. B; Comparison of Lewis lung carcinoma tumor growth within wild-type B6 or col a1 B6 transgenic mice; C; Wild-type B6 control mice were injected with Lewis lung carcinoma cells. Twenty-four hours later the mice were treated systematically with either Mab XL313 or an isotype matched control antibody (100 μg/per injection). Tumors were allowed to develop for 11 days and tumor sizes was monitored with calipers. Data represent the mean±standard errors of the tumor volumes from 5 mice per condition.

DESCRIPTION OF THE INVENTION

Collagens

Figure 1:
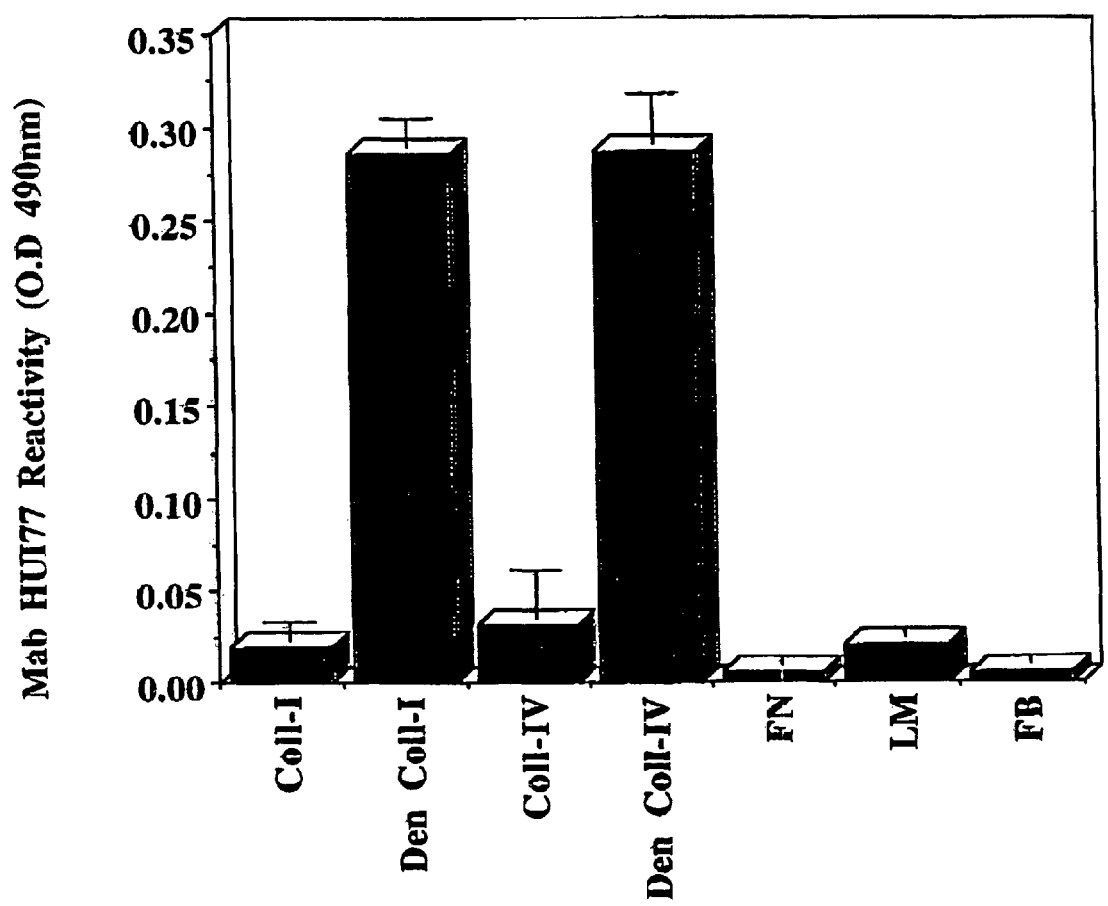
FIG. 1 illustrates Mab HUI77 reactivity with extracellular matrix components in solid phase ELISA. Microtiter plates (96 well) were coated with extracellular matrix components including native collagen type-I and type-IV, denatured collagen type-I and type-IV, vitronectin, fibronectin and fibrinogen, each at a concentration of 10 micrograms (ug) per milliliter (mL). Wells of the microtiter plate were blocked with 1% BSA in PBS for 1 hour at 37° C. Mab HUI77 was added to the wells at a concentration of 1 ug/mL and allowed to incubate for 2 hours at 37° C. After incubation, immunoreactivity was detected by incubation with goat anti-mouse peroxidase labeled secondary antibody. Immunoreactivity was measured with an ELISA plate reader at 490 nm using o-phenylenediamine as a substrate. Coll-I (native triple helical collagen type-I). Denatured Coll-I (Denatured Collagen type-I). Coll-IV (native triple helical collagen type-IV). Denatured Coll-IV (denatured collagen type-IV). VN (Vitronectin). FN (Fibronectin). FB (fibrinogen). Data bars represent the mean Optical Density (O.D)±standard deviations from triplicate wells.

The methods of the invention are suitable for use with a number of collagen molecules, including those from any animal. In one embodiment collagens are human collagens. Collagens may also be from any mammal such as rat, mouse, pig, rabbit etc. or from a bird such as chicken. Generally, a collagen is an extracellular matrix protein containing a $[Gly-Xaa-Xaa]_n$ sequence. Collagen types are well known in the art (see, e.g., Olsen, B. R. (1995) *Curr. Op. Cell. Biol.* 5:720-727; Kucharz, E. J. *The Collagens: Biochemistry and Pathophysiology*. Springer-Verlag, Berlin, 1992; Kunn, K. in *Structure and Function of Collagen* Types, eds. R. Mayne and R. E. Burgeson, Academic Press, Orlando). Human collagens are preferred collagens. Denatured collagen refers to collagen that has been treated such that it no longer predominantly assumes the native triple helical form. Denaturation can be accomplished by beating the collagen. In one embodiment, collagen is denatured by heating for about 15 minutes to about 100° C. Denaturation can also be accomplished by treating the collagen with a chaotropic agent. Suitable chaotropic agents include, for example, guanidinium salts. Denaturation of a collagen can be monitored, for example, by spectroscopic changes in optical properties such as absorbance, circular dichroism or fluorescence of the protein, by nuclear magnetic resonance, by Raman spectroscopy, or by any other suitable technique. Denatured collagen refers to denatured full length collagens as well as to fragments of collagen. A fragment of collagen can be any collagen sequence shorter than a native collagen sequences. For fragments of collagen with substantial native structure, denaturation can be effected as for a native full-length collagen. Fragments also can be of a size such that they do not possess significant native structure or possess regions without significant native structure of the native triple helical form. Such fragments are denatured all or in part without requiring the use of heat or of a chaotropic agent. The term denatured collagen encompasses proteolyzed collagen. Proteolyzed collagen refers to a collagen that has been fragmented through the action of a proteolytic enzyme. In particular, proteolyzed collagen can be prepared by treating the collagen with a metalloproteinase, such as MMP-1, MMP-2 or MMP-9, or by treating the collagen with a cellular extract containing collagen degrading activity or is that which occurs naturally at sites of neovascularization in a tissue.

A cryptic epitope within a collagen is a sequence that is not exposed for recognition within a native collagen, but is capable of being recognized by an antagonist of a denatured collagen. The sequence of cryptic epitopes can be identified by determining the specificity of an antagonist. Candidate cryptic epitopes also can be identified, for example, by examining the three dimensional structure of a native triple helical collagen. Peptide sequences that are not solvent exposed or are only partially solvent exposed in the native structure are potential cryptic epitopes.

An epitope is that amino acid sequence or sequences that are recognized by an antagonist of the invention. An epitope can be a linear peptide sequence or can be composed of noncontiguous amino acid sequences. An antagonist can recognize one or more sequences, therefore an epitope can define more than one distinct amino acid sequence target. The epitopes recognized by an antagonist can be determined by peptide mapping and sequence analysis techniques well known to one of skill in the art.

Antagonists

Antagonists of the invention bind to a denatured collagen but bind with substantially reduced affinity to the native form of the collagen. A "substantially reduced affinity" is an affinity of about 3-fold lower than that for the denatured collagen, more preferably, about 5-fold lower, and even more preferably about 10-fold lower, and even more preferably greater than 10-fold lower. Likewise, "substantially less" indicates a difference of at least about a 3 fold difference when referring to relative affinities. Antagonists are preferably specific for any one of the denatured collagens types-I, II, III, IV or V and combinations thereof. In one embodiment an antagonist binds to denatured collagen type-I but binds with substantially reduced affinity to native collagen type-I and to denatured collagens types II, III, IV and V. In another embodiment, an antagonist binds to denatured collagen type-IV but binds with substantially reduced affinity to native collagen type-IV. In another embodiment an antagonist binds to denatured collagens type-I, type-II, type-III, type-IV and type-V but binds with substantially reduced affinity to native collagens type-I, type-II, type-III, type-IV and type-V.

Apparent affinities can be determined by methods such as an enzyme linked immunosorbent assay (ELISA) or any other technique familiar to one of skill in the art. True affinities can be measured by techniques known to one of skill in the art.

In one embodiment, peptides containing epitopes recognized by an antagonist can be used themselves. In one embodiment, epitopes defined by the monoclonal antibodies HUI77, HUIV26 and XL313 are themselves used as antiangiogenic compositions.

Binding Assays

The invention also provides assay methods for identifying candidate denatured collagen antagonists for use according to the present methods. In these assay methods candidate antagonists are evaluated for their ability to bind both denatured collagen and native collagen, and furthermore can be evaluated for their potency in inhibiting angiogenesis in a tissue.

ELISA

The first assay measures binding of antagonists to denatured or native collagens in the solid phase by ELISA. The assay is useful with a variety of types of collagens, for example, the assay can be used with collagens types, I, II, III, IV and V as well as for other extracellular matrix components.

The assay also can be used to identify compounds which exhibit specificity for denatured but not native forms of collagen. The specificity assay is conducted by running parallel ELISAs where a potential antagonist is screened concurrently in separate assay chambers for the ability to bind denatured and native collagens.

Antagonists of denatured collagen can also be identified by their ability to compete for binding with an antagonist of the invention. For example, putative antagonists can be screened by monitoring their effect on the affinity of a known antagonist, such as HUI77, HUIV26 or XL313, in a binding assay, such as ELISA. Such antagonists likely have the same specificity as HUI77, and recognize the same cryptic epitope. Putative antagonists selected by such a screening method can bind either to the collagen or to the antagonist. Antagonists can be selected from the putative antagonists by conventional binding assays to determine those that bind to the denatured collagen epitope but not to the known antagonist.

Antagonists can also be identified by their ability to bind to a solid matrix containing a denatured collagen. Such putative antagonists are collected after altering solution conditions, such as salt concentration, pH, temperature, etc. The putative antagonists are further identified by their ability to pass through, under appropriate solution conditions, a solid matrix to which a native collagen has been affixed.

Angiogenesis Assays

Antagonists of the invention also can be assayed for their ability to modulate angiogenesis in a tissue. Any suitable assay known to one of skill in the art can be used to monitor such effects. Several such techniques are described herein.

The second assay measures angiogenesis in the chick chorioallantoic membrane (CAM) and is referred to as the CAM assay. The CAM assay has been described in detail by others, and further has been used to measure both angiogenesis and neovascularization of tumor tissues. See Ausprunk et al., *Am. J. Pathol.*, 79:597-618 (1975) and Ossonski et al., *Cancer Res.*, 40:2300-2309 (1980).

The CAM assay is a well recognized assay model for in vivo angiogenesis because neovascularization of whole tissue is occurring, and actual chick embryo blood vessels are growing into the CAM or into the tissue grown on the CAM.

As demonstrated herein, the CAM assay illustrates inhibition of neovascularization based on both the amount and extent of new vessel growth. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

A third assay measures angiogenesis is the in vivo rabbit eye model and is referred to as the rabbit eye assay. The rabbit eye assay has been described in detail by others, and further has been used to measure both angiogenesis and neovascularization in the presence of angiogenic inhibitors such as thalidomide. See D'Amato et al. (1994) *Proc. Natl. Acad. Sci.* 91:4082-4085.

The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent, and therefore the health of the rabbit is an indication of toxicity of the test reagent.

A fourth assay measures angiogenesis in the chimeric mouse:human mouse model and is referred to as the chimeric mouse assay. The assay has been described in detail by others, and further has been described herein to measure angiogenesis, neovascularization, and regression of tumor tissues. See Yan, et al. (1993) *J. Clin. Invest.* 91:986-996.

The chimeric mouse assay is a useful assay model for in vivo angiogenesis because the transplanted skin grafts closely resemble nonnal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. The chimeric mouse is exposed to any test reagent, and therefore the health of the mouse is an indication of toxicity.

Antibodies

The present invention describes, in one embodiment, denatured collagen antagonists in the form of antibodies which bind to denatured collagen but bind to native collagen with a substantially reduced affinity. Antibody antagonists also can inhibit angiogenesis. The invention also describes cell lines which produce the antibodies, methods for producing the cell lines, and methods for producing the monoclonal antibodies.

Antibodies of the invention can be monoclonal or polyclonal. In one embodiment, antibodies used are monoclonal. A monoclonal antibody of this invention comprises antibody molecules that immunoreact with isolated denatured collagen, but immunoreact with a substantially reduced affinity with the native form of the collagen. In one embodiment, an antibody of the invention recognizes denatured collagen type-I with an affinity at least about 3-fold, more preferably at least about 5-fold and most preferably at least about 10-fold higher than that for denatured collagen type-I. An antibody of the invention also can bind to preferably to denatured collagen type-IV and binds with substantially reduced affinity to native collagen type-IV. Antibodies of the invention also can bind to each of collagens types I, II, III, IV and V and bind to the native forms of each collagen with substantially reduced affinity.

Preferred monoclonal antibodies which preferentially bind to denatured collagen include monoclonal antibodies having the immunoreaction characteristics of mAb HUI77, mAb HUIV26 or mAb XL313.

Antibodies antagonists of the invention can be generated according to a number of methods known to one of skill in the art. For example, an animal can be immunized with a denatured collagen or fragment thereof. Antibodies thus generated can be selected both for their ability to bind to denatured proteolyzed collagen and for a substantially reduced affinity for the native form of the same collagen. Antibodies can, for example, be generated by the method of "subtractive immunization" (see, e.g., Brooks, P. C. et al. (1993) *J. Cell. Biol.* 122:1351-1359.)

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules and those portions of an immunoglobulin molecule that contain the paratope, including those portions known in the art as Fab, Fab', F(ab')$_2$ and F(v), and also referred to as antibody fragments.

In another preferred embodiment, the invention contemplates a truncated immunoglobulin molecule comprising a Fab fragment derived from a monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods.

For example, Fab and F(ab')$_2$ portions (fragments) of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions also are well known and are produced from F(ab') .sub.2 portions followed by reduction of the disulfide bonds linking the two heavy chain portions as with mercaptoethanol, and followed by alkylation of the resulting protein mercaptan with a reagent such as iodoacetamide. An antibody containing intact immunoglobulin molecules are preferred, and are utilized as illustrative herein.

The phrase "monoclonal antibody" in its various grammatical forms refers to a population of antibody molecules that contain only one species of antibody combining site capable of immunoreacting with a particular epitope. A monoclonal antibody may therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, Nature 256:495-497 (1975), which description is incorporated by reference. Additional methods are described by Zola, Monoclonal Antibodies: A Manual of Techniques, CRC Press, Inc. (1987). The hybridoma supernatant so prepared can be screened for the presence of antibody molecules that immunoreact with denatured collagens.

Briefly, to form the hybridoma from which the monoclonal antibody composition is produced, a myeloma or other self-perpetuating cell line is fused with lymphocytes obtained from the spleen of a mammal hyperimmunized with a source of denatured collagen.

It is preferred that the myeloma cell line used to prepare a hybridoma be from the same species as the lymphocytes. Typically, a mouse of the strain 129 G1 X.sup.+ is the preferred mammal. Suitable mouse myelomas for use in the present invention include the bypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to a selective growth medium, such as HAT (hypoxanthine aminopterin thymidine) medium. Hybridomas producing a monoclonal antibody of this invention are identified using the enzyme linked immunosorbent assay (ELISA) described in the Examples.

A monoclonal antibody of the present invention also can be produced by initiating a monoclonal hybridoma culture comprising a nutrient medium containing a hybridoma that secretes antibody molecules of the appropriate specificity. The culture is maintained under conditions and for a time period-sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396, 1959) supplemented with 4.5 g/L glucose, 20 nM glutamine, and 20% fetal calf serum. An exemplary inbred mouse strain is the Balb/c.

Other methods of producing a monoclonal antibody, a hybridoma cell, or a hybridoma cell culture also are well known. See, for example, the method of isolating monoclonal antibodies from an immunological repertoire as described by Sastry et al. (1989) *Proc. Natl. Acad. Sci. USA*, 86:5728-5732; and Huse et al. (1989) *Science*, 246:1275-1281.

Also contemplated by this invention is the hybridoma cell, and cultures containing hybridoma cells that produce monoclonal antibodies of this invention. Particularly preferred is a hybridoma cell line that secretes monoclonal antibody mAb HUI77, mAb HUIV26, or mAb XL313.

The invention contemplates, in one embodiment, a monoclonal antibody that has the immunoreaction characteristics of Mab HUI77, Mab HUIV26, or Mab XL313.

It also is possible to determine, without undue experimentation, if a monoclonal antibody has an equivalent specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides are well known in the art. This does not suggest that antibodies with distinct CDR regions cannot bind to the same epitope.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

Use of the term "having the binding specificity of" indicates that equivalent monoclonal antibodies exhibit the same or similar immunoreaction (binding) characteristics and compete for binding to a preselected target epitope.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention.

Thus, the invention contemplates, in one embodiment, a monoclonal antibody of this invention that is humanized by grafting to introduce components of the human immune system without substantially interfering with the ability of the antibody to bind antigen.

The antibody of the invention can also be a fully human antibody such as those generated, for example, by selection from an antibody phage display library displaying human single chain or double chain antibodies such as those described in de Haard, H. J. et al. (1999) *J. Biol. Chem.* 274:18218-30 and in Winter, G. et al. (1994) *Annu. Rev. Immunol.* 12:433-55.

Polypeptides

Antagonists of denatured collagen also can be polypeptides or peptides. The term polypeptide refers to a sequence of 3 or more amino acids connected to one another by peptide bonds between the alpha-amino group and carboxy group of contiguous amino acid residues. The term peptide as used herein refers to a linear series of two or more connected one to the other as in a polypeptide.

In one embodiment, the invention contemplates denatured collagen antagonists in the form of polypeptides. A polypeptide antagonist of denatured collagen can be any peptide or polypeptide capable of binding to a denatured collagen, but binds to the native form of the collagen with substantially reduced affinity.

The identification of preferred denatured collagen antagonist peptides having selectivity for denatured collagen can readily be identified in a typical inhibition of binding assay, such as the ELISA assay described in the Examples.

Peptide and polypeptide antagonists can be generated by a number of techniques known to one of skill in the art. For example, a two hybrid system (e.g., Fields, S. (1989) *Nature* 340:245-6) can use a fragment of a collagen as "bait" for selecting protein antagonists from a library that bind to the collagen peptide. The library of potential antagonists can be derived from a cDNA library, for example. In another embodiment, the potential antagonists can be variants of known collagen binding proteins. Such proteins can be randomly mutagenized or subjected to gene shuffling, or other available techniques for generating sequence diversity.

Peptide and polypeptide antagonists of the invention also can be generated by techniques of molecular evolution. Libraries of proteins can be generated by mutagenesis, gene shuffling or other available techniques for generating molecular diversity. Protein pools representing numerous variants can be selected for their ability to bind to denatured collagen, for instance by passing such protein pools over a solid matrix to which a denatured collagen has been attached. Elution with gradients of salt, for example, can provide purification of variants with affinity for the denatured collagen. A negative selection step also can be included whereby such pools are passed over a solid matrix to which native collagens have been attached. The filtrate will contain those variants within the pool that have a reduced affinity for the native form of the collagen.

Peptide and polypeptide antagonists of the invention also can be generated by phage display. A randomized peptide or protein can be expressed on the surface of a phagemid particle as a fusion with a phage coat protein. Techniques of monovalent phage display are widely available (see, e.g., Lowman H. B. et al. (1991) *Biochemistry* 30:10832-8.) Phage expressing randomized peptide or protein libraries can be panned with a solid matrix to which a native collagen molecule has been attached. Remaining phage do not bind native collagens, or bind native collagens with substantially reduced affinity. The phage are then panned against a solid matrix to which a denatured collagen has been attached. Bound phage are isolated and separated from the solid matrix by either a change in solution conditions or, for a suitably designed construct, by proteolytic cleavage of a linker region connecting the phage coat protein with the randomized peptide or protein library. The isolated phage can be sequenced to determine the identity of the selected antagonist.

In another embodiment, a polypeptide includes any analog, fragment or chemical derivative of a polypeptide whose amino acid residue sequence is shown herein so long as the polypeptide is an antagonist of denatured collagen, but not of native collagen. Therefore, a present polypeptide can be subject to various changes, substitutions, insertions, and deletions where such changes provide for certain advantages in its use. In this regard, a denatured collagen antagonist polypeptide of this invention corresponds to, rather than is identical to, the sequence of a recited peptide where one or more changes are made and it retains the ability to function as a denatured collagen antagonist in one or more of the assays as defined herein.

Thus, a polypeptide can be in any of a variety of forms of peptide derivatives, that include amides, conjugates with proteins, cyclized peptides, polymerized peptides, analogs, fragments, chemically modified peptides, and like derivatives.

Other Antagonists

Antagonists of the invention also can be small organic molecules, such as those natural products, or those compounds synthesized by conventional organic synthesis or combinatorial organic synthesis. Compounds can be tested for their ability to bind to a denatured collagen for example by using the column binding technique described above. Compounds also are selected for reduced affinity for the native form of the collagen by a similar column binding technique.

Antagonists of the invention also can be non-peptidic compounds. Suitable non-peptidic compounds include, for example, oligonucleotides. Oligonucleotides as used herein refers to any heteropolymeric material containing purine, pyrimidine and other aromatic bases. DNA and RNA oligonucleotides are suitable for use with the invention, as are oligonucleotides with sugar (e.g., 2' alkylated riboses) and backbone modifications (e.g., phosphorothioate oligonucleotides). Oligonucleotides may present commonly found purine and pyrimidine bases such as adenine, thymine, guanine, cytidine and uridine, as well as bases modified within the heterocyclic ring portion (e.g., 7-deazaguanine) or in exocyclic positions. Oligonucleotide also encompasses heteropolymers with distinct structures that also present aromatic bases, including polyamide nucleic acids and the like.

An oligonucleotide antagonist of the invention can be generated by a number of methods known to one of skill in the art. In one embodiment, a pool of oligonucleotides is generated containing a large number of sequences. Pools can be generated, for example, by solid phase synthesis using mixtures of monomers at an elongation step. The pool of oligonucleotides is sorted by passing a solution containing the pool over a solid matrix to which a denatured collagen or fragment thereof has been affixed. Sequences within the pool that bind to the denatured collagen are retained on the solid matrix. These sequences are eluted with a solution of different salt concentration or pH. Sequences selected are subjected to a second selection step. The selected pool is passed over a second solid matrix to which native collagen has been affixed. The column retains those sequences that bind to the native collagen, thus enriching the pool for sequences specific for the denatured collagen. The pool can be amplified and, if necessary, mutagenized and the process repeated until the pool shows the characteristics of an antagonist of the invention. Individual antagonists can be identified by sequencing members of the oligonucleotide pool, usually after cloning said sequences into a host organism such as *E. coli*.

Disease Treatment

The present invention relates generally to the discovery that ligation of certain epitopes in denatured collagens but not of native collagens inhibits angiogenesis. This discovery is important because of the role that angiogenesis plays in a variety of disease processes. By inhibiting angiogenesis, one can intervene in the disease, ameliorate the symptoms, and in some cases cure the disease.

Where the growth of new blood vessels is the cause of, or contributes to, the pathology associated with a disease, inhibition of angiogenesis will reduce the deleterious effects of the disease. Examples include psoriasis, rheumatoid arthritis, diabetic retinopathy, inflammatory diseases, restenosis, macular degeneration and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

The methods of the present invention are effective in part because the therapy is highly selective for angiogenesis and not other biological processes. As shown in the Examples, only new vessel growth is inhibited by antagonists of denatured collagens, and therefore the therapeutic methods do not adversely effect mature vessels. Also as shown in the Examples, an antagonist binds to angiogenic sites in tumors but not to normal surrounding tissues.

The discovery that ligation of denatured collagens alone can effectively inhibit angiogenesis allows for the development of therapeutic compositions with potentially high specificity, and therefore relatively low toxicity. Thus although the invention discloses the use of antibody-based antagonists which have the ability to ligate one or more denatured collagens, one can design other antagonists that also can specifically ligate denatured collagens, but not native collagens.

Prior to the discoveries of the present invention, it was not known that angiogenesis, and any of the processes dependent on angiogenesis, could be inhibited in vivo by the use of reagents that antagonize cryptic epitopes in collagens, i.e. those that are found in proteolyzed or denatured collagens, but not in native forms of the same collagens.

Methods for Inhibition of Angiogenesis

The invention provides for a method for the inhibition of angiogenesis in a tissue, and thereby inhibiting events in the tissue which depend upon angiogenesis. Generally, the method comprises administering to the tissue a composition comprising an angiogenesis-inhibiting amount of a denatured collagen antagonist.

As described earlier, angiogenesis includes a variety of processes involving neovascularization of a tissue including "sprouting", vasculogenesis, or vessel enlargement, all of which angiogenesis processes involve disruption of extracellular matrix collagen in blood vessels. With the exception of traumatic wound healing, corpus leuteum formation and embryogenesis, it is believed that the majority of angiogenesis processes are associated with disease processes and therefore the use of the present therapeutic methods are selective for the disease.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi's sarcoma and the like cancers which require neovascularization to support tumor growth. Other suitable tumors include melanoma, carcinoma, sarcoma, fibrosarcoma, glioma and astrocytoma.

Thus, methods which inhibit angiogenesis in a diseased tissue ameliorate symptoms of the disease and, depending upon the disease, can contribute to cure of the disease. In one embodiment, the invention contemplates inhibition of angiogenesis, per se, in a tissue. The extent of angiogenesis in a tissue, and therefore the extent of inhibition achieved by the present methods, can be evaluated by a variety of methods, such as are described in the Examples for detecting proteolyzed or denatured collagen-immunopositive immature and nascent vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli. Tissue, as used herein, also encompasses all bodily fluids, secretions and the like, such as serum, blood, cerebrospinal fluid, plasma, urine, synovial fluid, vitreous humor.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species. Such a patient can be, for example, a pig, a cow, a horse, a goat, a sheep, a mule, a donkey, a dog, a cat, a rabbit, a mouse and a rat.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, Kaposi's Sarcoma and the like tissues. Exemplary tumor tissue angiogenesis, and inhibition thereof, is described in the Examples.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis according to the present methods. Similarly, the invention provides a method of inhibiting tumor growth by practicing the angiogenesis-inhibiting methods.

The methods also are particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods also can apply to inhibition of tumor tissue growth, to inhibition of tumor metastases formation, and to regression of established tumors.

Restenosis is a process of smooth muscle cell (SMC) migration arid proliferation at the site of percutaneous transluminal coronary angioplasty which hampers the success of angioplasty. The migration and proliferation of SMCs associated with blood vessels during restenosis is related to the process of angiogenesis which is inhibited by the present methods. Therefore, the invention also contemplates inhibition of restenosis by inhibiting angiogenic related processes according to the present methods in a patient following angioplasty procedures. For inhibition of restenosis, the denatuted collagen antagonist is typically administered after the angioplasty procedure for from about 2 to about 28 days, and more typically for about the first 14 days following the procedure.

The present method for inhibiting angiogenesis in a tissue, and therefore for also practicing the methods for treatment of angiogenesis-related diseases, comprises contacting a tissue in which angiogenesis is occurring, or is at risk for occurring, with a composition comprising a therapeutically effective amount of a denatured collagen antagonist capable of binding to denatured or proteolyzed collagen, but not to native forms of the collagen. Thus, the method comprises administering to a patient a therapeutically effective amount of a physiologically tolerable composition containing an denatured collagen antagonist of the invention.

The dosage ranges for the administration of the denatured collagen antagonist depend upon the form of the antagonist, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The, dosage also can be adjusted by the individual physician in the event of any complication.

A therapeutically effective amount is an amount of denatured collagen antagonist sufficient to produce a measurable inhibition of angiogenesis in the tissue being treated, i.e., an angiogenesis-inhibiting amount. Inhibition of angiogenesis can be measured in situ by immunohistochemistry, as described herein, or by other methods known to one skilled in the art.

Potency of a denatured collagen antagonist can be measured by a variety of means including inhibition of angiogenesis in the CAM assay, in the in vivo rabbit eye assay, in the in vivo chimeric mouse: human assay and the like assays.

A therapeutically effective amount of a denatured collagen antagonist of this invention in the form of a monoclonal antibody is typically an amount such that when administered in a physiologically tolerable composition is sufficient to achieve a plasma concentration of from about 0.01 microgram (ug) per milliliter (mL) to about 100 ug/mL, preferably from about 1 ug/mL to about 5 ug/mL, and usually about 5 ug/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Where the antagonist is in the form of a fragment of a monoclonal antibody, the amount can readily be adjusted based on the mass of the fragment relative to the mass of the whole antibody. A preferred plasma concentration in molarity is from about 2 micromolar (uM) to about 5 millimolar (mM) and preferably about 100 uM to 1 mM antibody antagonist.

A therapeutically effective amount of a denatured collagen antagonist of this invention in the form of a polypeptide, or small molecule, is typically an amount of polypeptide such that when administered in a physiologically tolerable composition is sufficient to achieve a plasma concentration of from about 0.1 microgram (ug) per milliliter (mL) to about 200 ug/mL, preferably from about 1 ug/mL to about 150 ug/mL. Based on a polypeptide having a mass of about 500 grams per mole, the preferred plasma concentration in molarity is from about 2 micromolar (uM) to about 5 millimolar (mM) and preferably about 100 uM to 1 mM polypeptide antagonist. Stated differently, the dosage per body weight can vary from about 0.1 mg/kg to about 300 mg/kg, and preferably from about 0.2 mg/kg to about 200 mg/kg, in one or more dose administrations daily, for one or several days.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, antagonists including monoclonal antibodies, polypeptides, and derivatives thereof can be administered intravenously, intraperitoneally, intramuscularly, subcutaneously, intracavity, transdermally, topically, intraocularly, orally, intranasally and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

In one preferred embodiment as shown in the Examples, the denatured collagen antagonist is administered in a single dosage intravenously.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As demonstrated by the present Examples, inhibition of angiogenesis and tumor regression occurs as early as 7 days after the initial contacting with antagonist. Additional or prolonged exposure to antagonist is preferable for 7 days to 6 weeks, preferably about 14 to 28 days.

Therapeutic Compositions

The present invention contemplates therapeutic compositions useful for practicing the therapeutic methods described herein. Therapeutic compositions of the present invention contain a physiologically tolerable carrier together with an denature or proteolyzed collagen antagonist as described herein, dissolved or dispersed therein as an active ingredient. In a preferred embodiment, the therapeutic denatured collagen antagonist composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting amount of an denatured collagen antagonist of the present invention, typically formulated to contain an amount of at least 0.1 weight percent of antagonist per weight of total therapeutic composition. A weight percent is a ratio by weight of inhibitor to total composition. Thus, for example, 0.1 weight percent is 0.1 grams of inhibitor per 100 grams of total composition.

An antibody can be conjugated with cytotoxins, cytotoxic agents, fro delivery to a to tumor or other tissue undergoing angiogenesis. Such conjugates can be made with a cytolysin or an exotoxin, for example ricin A, diphtheria toxin A, or *Pseudomonas* exotoxin and fragments thereof. The cytotoxic agent can also be a radioactively labeled with an isotope so as to locally deliver a toxic dose of radioactivity to an angiogenic tissue.

Antagonists of the invention can also be used to deliver an enzyme to a target wherein the enzyme is capable of converting a prodrug into an active form of the drug. antibody-directed enzyme activated prodrug therapy (ADEPT) (see, e.g., Syrigos, K. N. (1999) *Anticancer Res.* 19:605-13). Briefly, an antagonist of the invention is conjugated with an enzyme, such as a lactamase, protease or esterase, that can convert a non-toxic or inactive prodrug into a toxic or active drug. Because the antagonist of the invention localizes to sites of angiogenesis, and particularly to sites of tumors or metastases, toxic drugs can be directed to the Detection Methods Antagonists of the invention also are suitable for detection of angiogenesis in tissues.

For example, where the antagonist is an antibody, the antagonist can be used in immunohistochemical techniques to stain tissues ex vivo. Immunological techniques such as immunostaining and ELISA are described in, for example, *Receptor Binding Techniques, Methods in Molecular Biology*. 106. ed. M. Keen. Humana Press, 1999; Brooks et al. (1998) *Cell* 92:391-400; Brooks et al. (1996) *Cell* 85:683-693; and Brooks et al. (1993) *J. Cell. Biol.* 122:1351-1359.

The antagonist of the invention, once bound to the target tissue can be detected either directly or indirectly. Direct detection can be preformed on antagonists that comprise a detectable label such as a fluorochrome, a radioactive tag, paramagnetic heavy metal or diagnostic dye.

Alternatively, detection can occur through a secondary interaction. For example, a detectably labeled antibody that recognizes the antagonist can be used to visualize the location of the antagonist. For example, if the antagonist is a monoclonal antibody of mouse origin, a goat anti-mouse antibody that is suitably labeled can be used. The Examples describe the use, for example, of a goat anti-mouse peroxidase conjugated antibody. One of skill in the art can determine suitable secondary antibodies for use with various antagonists.

For in vivo detection, it is preferable to use a detectably labeled antagonist. The labeled antagonist is administered to a patient intravenously, intramuscularly, etc . . . Labels suitable for detection within a patient are particularly preferred. For example, paramagnetically labeled can be detected by magnetic resonance imaging. Radioactively tagged antagonists also can be detected.

EXAMPLES

Example 1

Monoclonal Antibody HUI77

This example describes the generation of a denatured collagen specific monoclonal antibody, Mab HUI77.

Mab HUI77 was generated and isolated by the immunological technique termed subtractive immunization (S.I). The subtractive immunization technique allows one to experimentally manipulate the immune response within mice to selectively enhance an immune response to a rare and/or low abundant epitope within a mixture of common highly antigenic epitopes. Briefly, female BALB/c mice were injected intraperitoneally with either native human triple helical collagen type-I or type-IV. At 24 and 48 hours following the injections of triple helical collagen, the mice were injected with the tolerizing agent cyclophosphamide to kill activated B-cells that would produce antibodies directed to common immunodominant epitopes within native triple helical collagen type-I and type-IV. Following the tolerization protocol, the mice were next injected with thermally denatured human collagen type-I or type-IV to stimulate an immune response to epitopes exposed following thermal denaturation. Collagen was denatured by boiling for 15 minutes. The injections of thermally denatured collagen type-I and type-IV were given every three weeks for a total of 4 to 5 injections. Sera from each mouse was tested for immunoreactivity with both native triple helical and denatured collagens. The mice demonstrating the highest titer for reactivity to denatured collagen as compared to triple helical collagen were used for the production of hybridomas. Spleen cells from the selected mice were fused with myeloma cells by standard techniques. Individual hybridoma clones were tested for the production of antibody to either triple helical or denatured collagen type-I and type-IV. Hybridoma clones were selected that produced antibodies that demonstrated a selective reactivity to denatured collagen type-I or type-IV as compared to native triple helical collagens type-I and type-IV. Mabs were purified by standard techniques.

As shown in FIG. 1, HUI77 was shown to specifically recognize denatured collagens type-I and type-IV but binds to native triple helical collagens type-I and type-IV with substantially reduced affinity. In particular, HUI77 binds to denatured collagen type-I with an apparent reactivity of at least about 10-fold higher than that of native collagen type-I as measured by ELISA. HUI77 also binds to denatured collagen type-IV with an affinity of about 10-fold higher than for native collagen type-IV. In addition, Mab HUI77 does not bind substantially to, other matrix components such as laminin, fibronectin, vitronectin or fibrinogen, thus demonstrating its specificity to a cryptic epitope within collagens type-I and type-IV.

Figure 2:
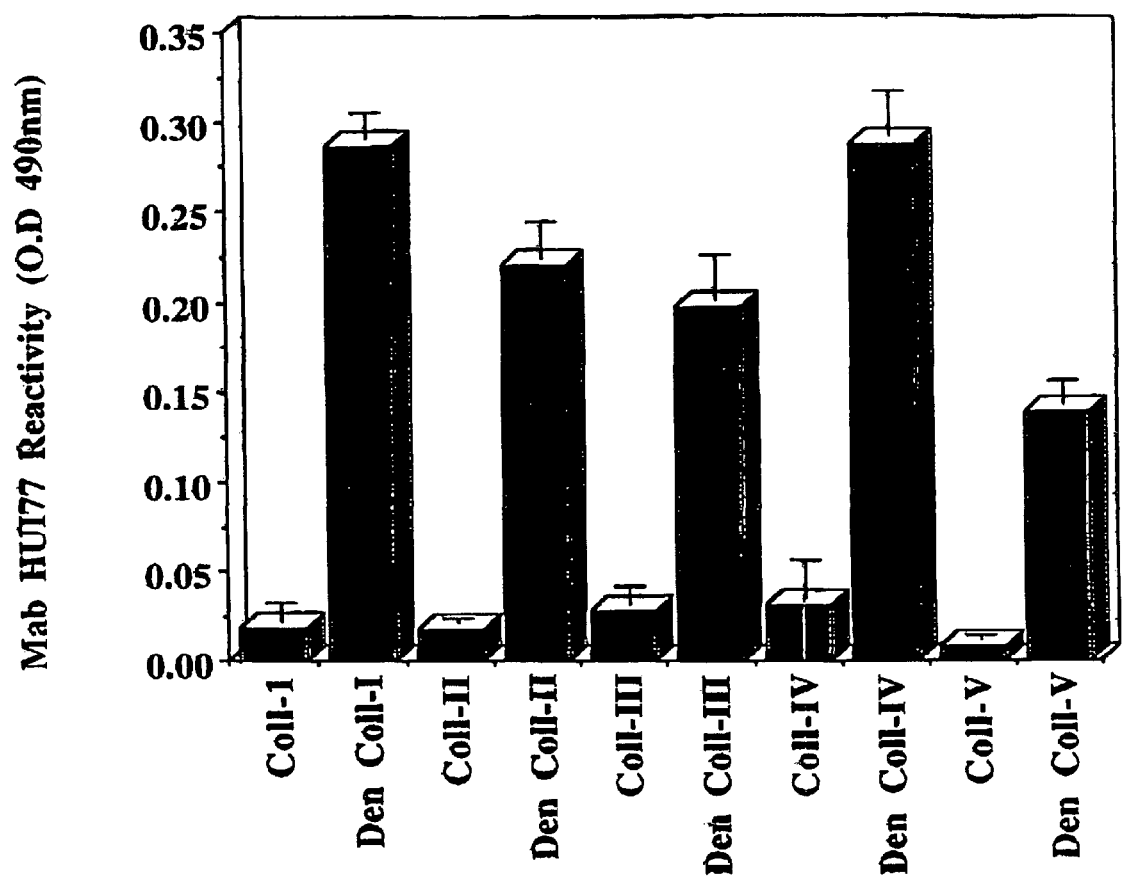
FIG. 2 demonstrates Mab HUI77 reactivity with genetically distinct forms of collagen. Microtiter plates were coated with distinct forms of collagen at a concentration of 10 μg/mL. Wells of the microtiter plates were blocked with 1% BSA in PBS for 1 hour at 37° C. Immunoreactivity was detected by incubation with goat anti-mouse peroxidase labeled secondary antibody. Immunoreactivity was measured by determining the optical density with an ELISA plate reader at 490 nm. Coll-I; triple helical Collagen-I. Den Coll-I; denatured Collagen-I. Coll-II; triple helical Collagen-II. Den Coll-II; denatured Collagen-II. Coll-III; triple helical Collagen-III. Den Coll-III; denatured Collagen-III. Coll-IV; triple helical Collagen-IV. Den Coll-IV; denatured Collagen-IV. Coll-V; triple helical Collagen-V. Den Coll-V; denatured Collagen-V. Data bars represent the mean O.D.±standard deviation from triplicate wells.

Mab HUI77 also is specific for other denatured collagens and binds the native forms of these collagens with substantially reduced affinity. As shown in FIG. 2, HUI77 also binds denatured collagens III, IV and V with about 7-fold, about 8-fold, and about 10-fold more tightly than the respective native forms of these collagens using ELISA.

Example 2

Detection of Solid Tumors

This example shows that antagonists of the invention can be used to detect denatured collagens in tumorous tissue. Monoclonal antibody HUI77, described in Example 1, was used to indirectly immunostain normal and tumorous tissue. As shown in FIG. 3, indirect immunofluoresence analysis using Mab HUI77 of human melanoma tumor biopsies as well as of M21 melanoma tumor grown in full thickness human skin indicate the generation of denatured forms of collagens associated with human melanoma tumors in vivo. Importantly, little if any evidence of denatured collagen was detected in normal tissues in the absence of tumors, suggesting that denatured collagen may be a specific marker of solid human tumors.

Example 3

Detection of Angiogenesis in Human Tumors

This example demonstrates that antagonists of the invention can be used to detect angiogenesis in human tumors.

Indirect immunofluoresence analysis, shown in FIG. 4, of human melanoma tumor biopsies demonstrates the generation and localization of denatured collagen surrounding human tumor associated blood vessels in vivo. Importantly, little if any evidence of denatured collagen was detected with Mab HUI77 surrounding normal blood vessels in the absence of tumors, suggesting that denatured collagen may be a specific marker of angiogenic tumor associated blood vessels.

Example 4

Antagonists Inhibit Endothelial Cell Adhesion and Migration

This example demonstrates that certain antagonists of the invention can inhibit human endothelial cell adhesion to denatured collagens.

Figure 5:
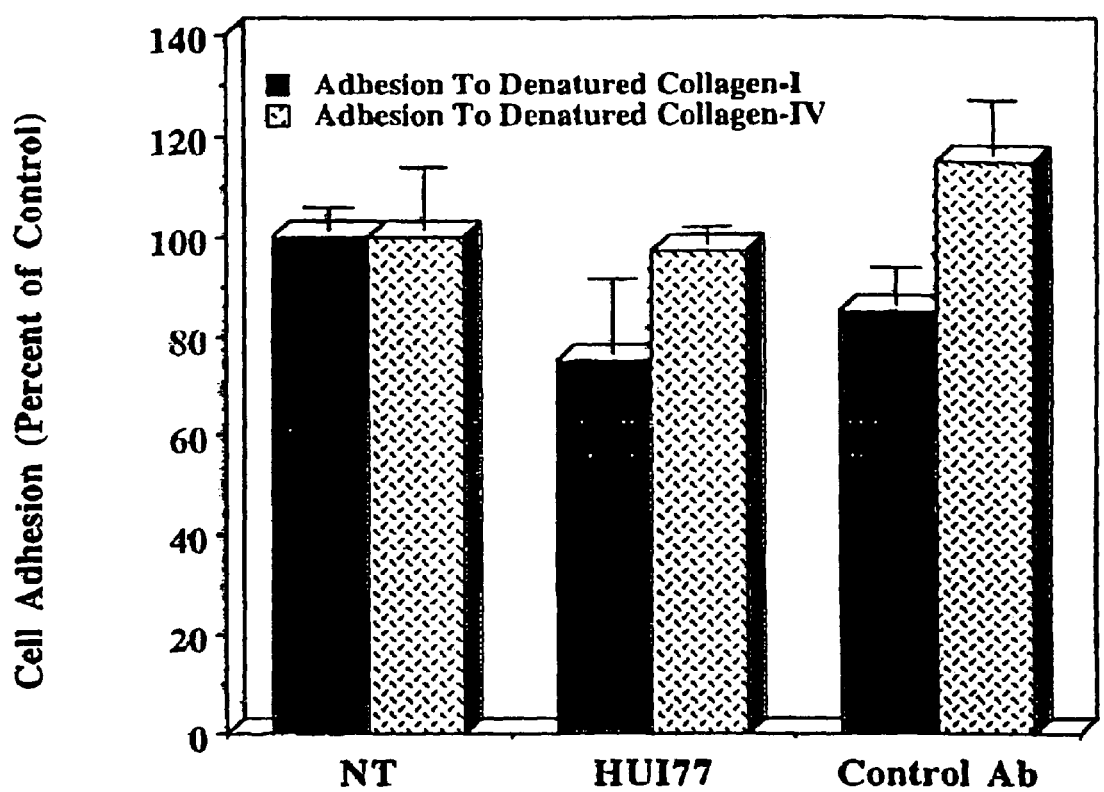
FIG. 5 demonstrates the effects of Mab HUI77 on human endothelial cell adhesion. Microtiter plates (96 wells) were coated with either native or denatured collagen type-I or type-IV at a concentration of 10 μg/mL. Wells of the microtiter plate were blocked with 1% BSA in PBS for 1 hour at 37° C. Human endothelial cells (HUVECs) were then allowed to attach to the coated wells in the presence or absence of purified Mab HUI77 (50 μg/mL) or an isotype matched control antibody at a concentration of 50 ug/mL for 30 minutes. The non-attached cells were removed by washing and the attached cells were stained with crystal violet. Cell adhesion was quantified by measuring the optical density (O.D.) of eluted dye at 600 nm. Data Bars represent the mean O.D±standard deviation from triplicate wells. Data are represented as percent of control.

Mab HUI77 showed the capacity to inhibit human endothelial cell adhesion to denatured collagen type-I by approximately 40% as compared to control antibody. These findings, summarized in FIG. 5, suggest that Mab HUI77 binds to a cryptic epitope within collagen type-I that is at least partially involved in endothelial cell adhesion to denatured collagen-I. Since endothelial cell adhesive processes are thought to play a role in tumor growth and angiogenesis, this function blocking antibody may have an effect on angiogenesis and tumor growth in vivo.

Figure 6:
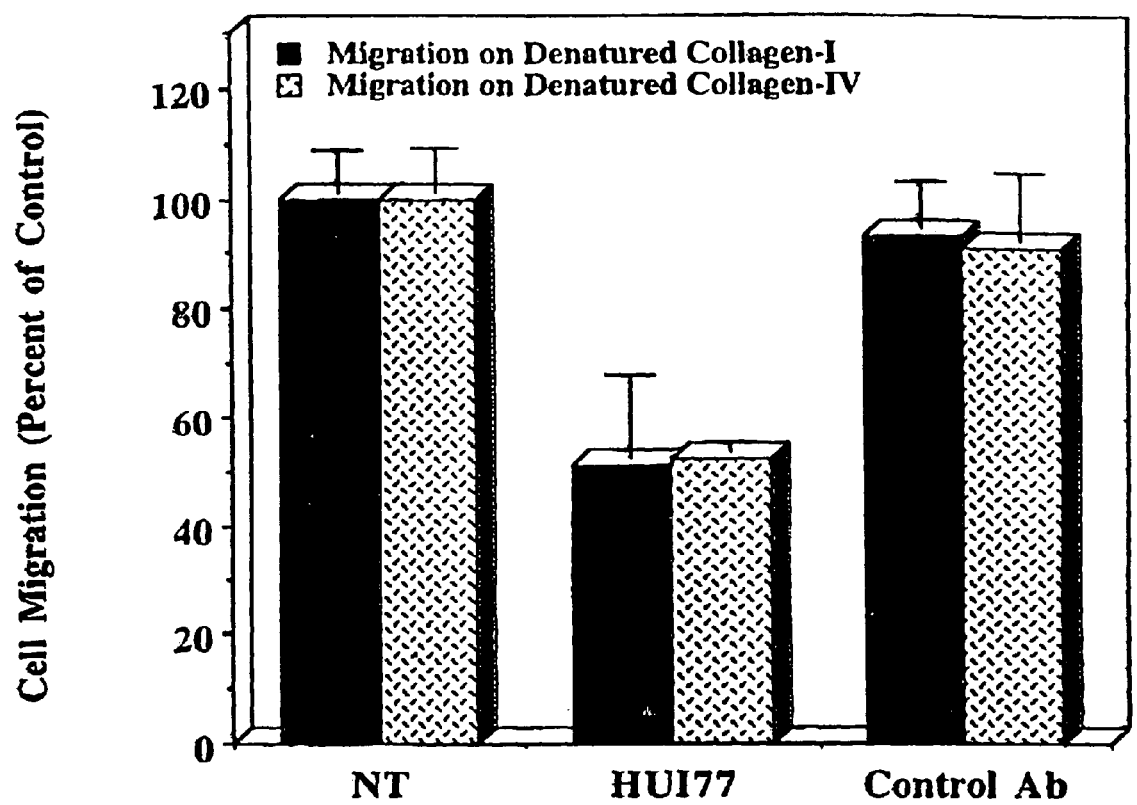
FIG. 6 demonstrates the effects of Mab HUI77 on human endothelial cell migration. Membranes from transwell migration chambers were coated with either denatured collagen type-I or type-IV at a concentration of 25 µg/mL. Human endothelial cells (HUVECs) were allowed to migrate in the presence or absence of purified Mab HUI77 or an isotype matched control antibody (100 ug/mL) for a total of 6 hours. Cells remaining on the top side of the membrane were removed and the cells which had migrated to the underside of the membrane were stained with crystal violet. Cell migration was quantified by measuring the optical density (O.D) of eluted dye at 600 nm with a microplate reader. Data Bars represent the mean O.D±standard deviation from triplicate wells. Data are expressed as percent of control.

Mab HUI77 also showed the capacity to inhibit human endothelial cell migration on denatured collagen-I by approximately 80% as compared to either control antibody or no treatment, as shown in FIG. 6. These findings suggest that Mab HUI77 binds to a cryptic epitope within collagen type-I that plays a significant role in cellular migration on denatured collagen-I. Given that cell migration is thought to play a important role in tumor metastasis and angiogenesis, and that denatured collagen was detected in association with malignant tumor cells and angiogenic blood vessels, this function blocking antibody may have a significant impact on angiogenesis and tumor growth and metastasis in vivo.

Example 6

Inhibition of Angiogenesis by Monoclonal Antibody HUI77

This example shows that antagonists of the invention effectively inhibit angiogenesis in the chick CAM assay.

Figure 7:
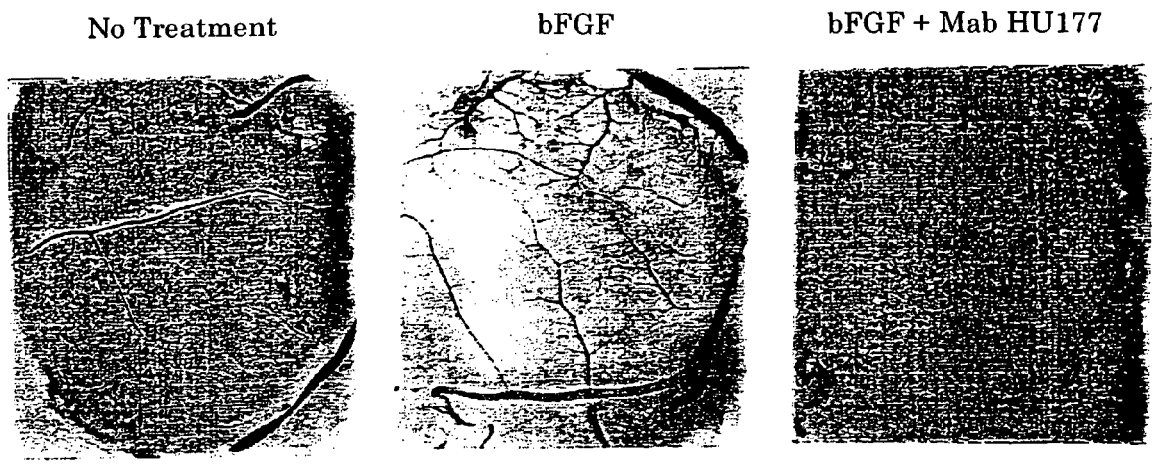
FIG. 7 demonstrates the effects of systemic administration of purified Mab HUI77 on angiogenesis in vivo. Filter discs saturated with βFGF were placed on the Chorioallantoic membranes (CAMs) of 10 day old chick embryos. Twenty four hours later the embryos received a single intravenous injection with 20 ug of Mab HUI77 or a control. At the end of a 3 day incubation period the filter discs and surrounding CAM tissues were removed and angiogenesis was quantified by counting the number of blood vessel branch points within the area of the filter disc. Examples of CAM tissue from a typical experiment are shown.
Figure 8:
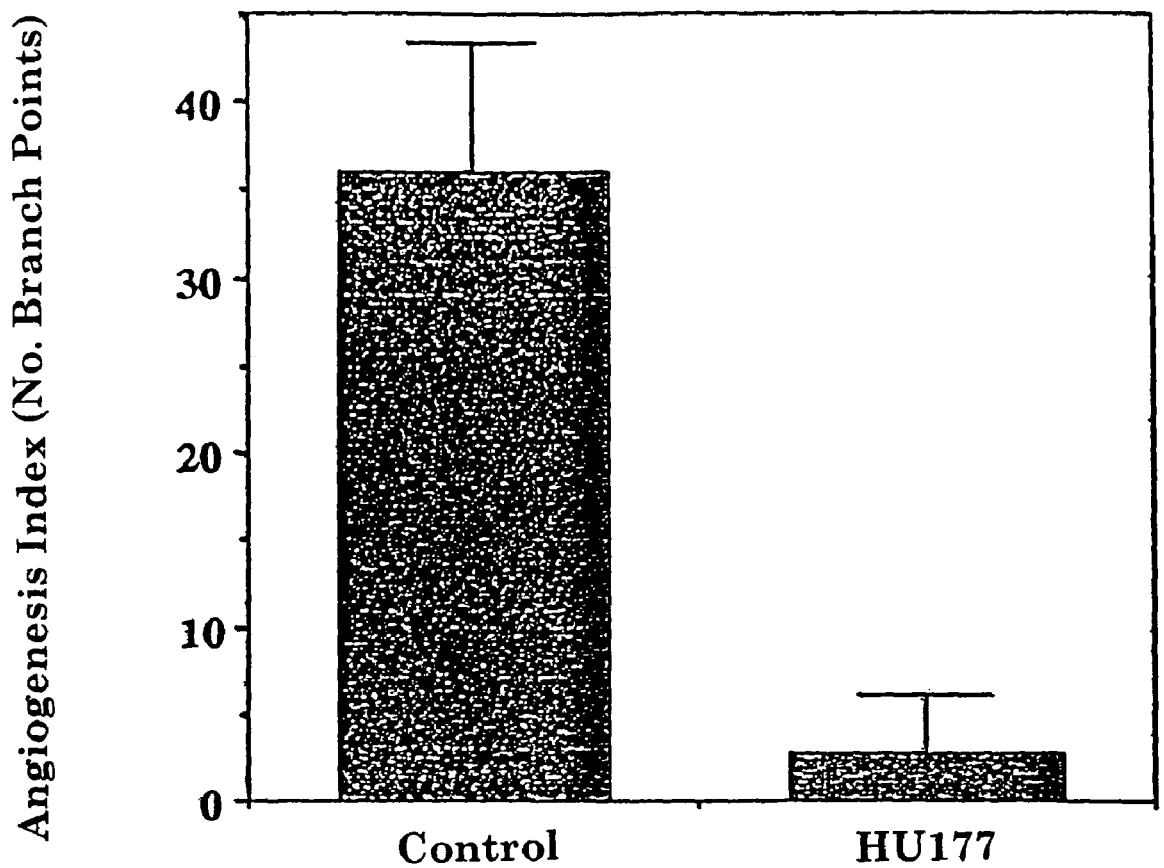
FIG. 8 shows the quantification of the angiogenesis experiments with Mab HUI77. Data bars represent the mean±standard errors of 5 to 10 embryos per condition. Angiogenesis index is equal to the number of branch points from experimentally treated embryos minus the number of branch points form CAMs in the absence of βFGF.

Furthermore, systemic administration of Mab HUI77 inhibited βFGF induced angiogenesis by approximately 90% as compared to controls (FIGS. 7 and 8). Angiogenic index was measured by counting the number of blood vessel branch points in the chick CAM assay (FIG. 8). Importantly, no toxic side effects were noted in the embryos during the assay period. Moreover, few if any effects from this Mab were noted on normal quiescent blood vessels. It is possible that much lower concentration of Mab might be used and result in similar effects. These findings indicate that Mab HUI77 is a potent anti-angiogenic reagent that may have significant clinical applications.

Example 7

Inhibition of Tumor Growth by Mab HUI77

This example shows that antagonists of the invention effectively inhibit tumor growth in melanoma tumors in vivo.

Figure 9:
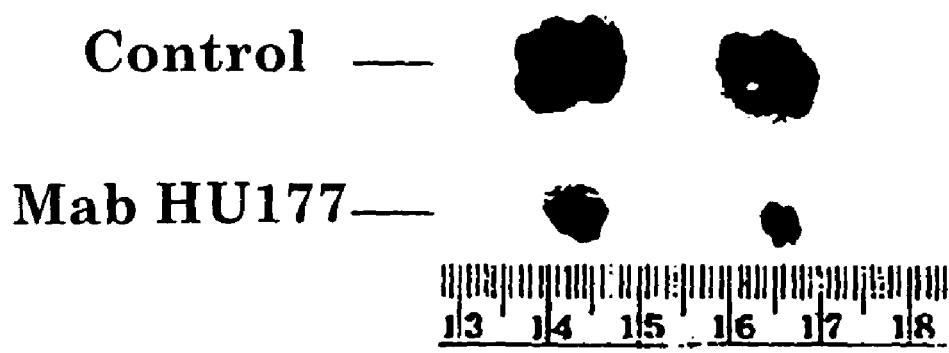
FIG. 9 shows the effects of systemic administration of purified Mab HUI77 on tumor-growth in vivo. A). CS-1 melanoma tumor cells ($5 \times 10^6$) were inoculated on the CAMs of 10 day old chick embryos. Twenty four hours later the embryos received a single intravenous injection of 100 ug of purified Mab HUI77 or control. The embryos were allowed to incubate for a total of 7 days. At the end of the 7 day incubation period, the resulting tumors were resected and wet weights determined. Photographs show representative tumors taken from embryos treated with or without Mab HUI77.
Figure 10:
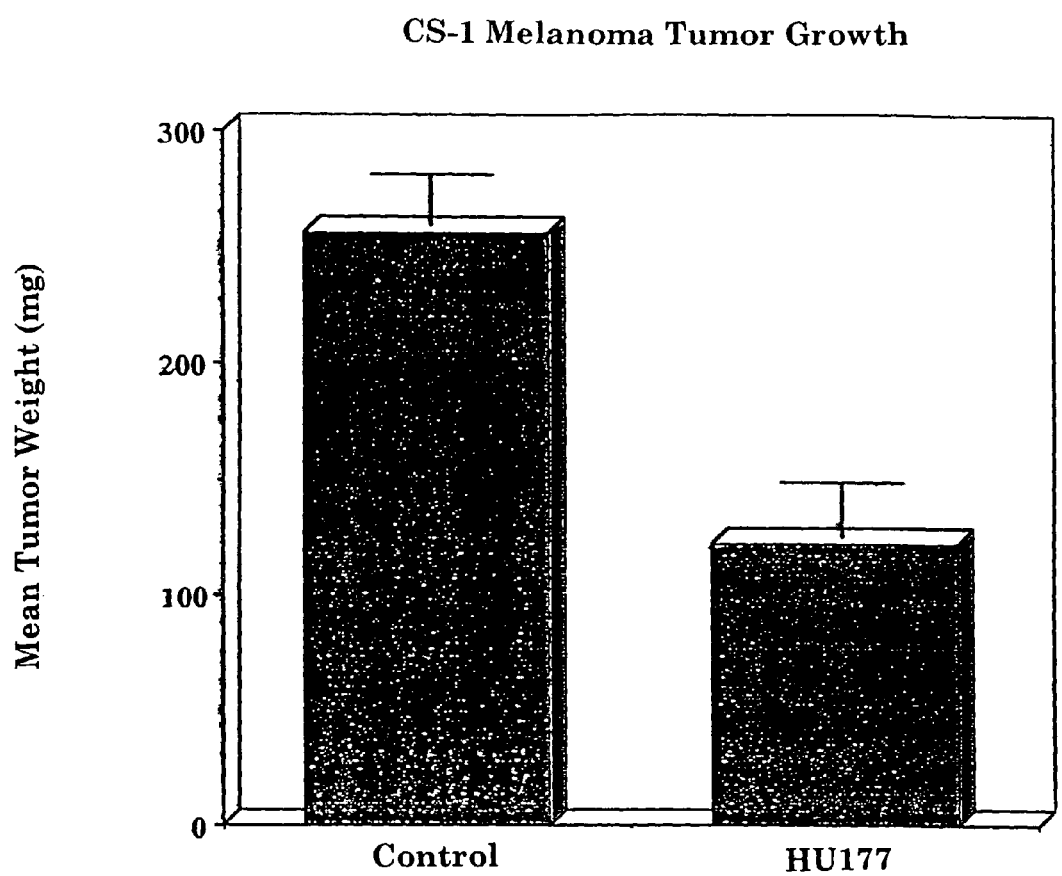
FIG. 10 shows the quantification of the wet weight of the tumors. Data bars represent the mean±the standard errors of the tumor weights from 5 to 12 embryos per condition.

Systemic administration of Mab HUI77 inhibited Melanoma tumor growth by approximately 53% as compared to controls, as shown in FIGS. 9 and 10. Importantly, no toxic side effects were noted in the embryos during the assay period. Moreover, little if any effects from this Mab were noted on adjacent tissue. It is possible that much lower concentration of Mab might be used and result in similar effects.

These findings indicate that Mab HUI77 is a potent anti-tumor reagent that may have significant clinical applications.

Example 8

Monoclonal Antibody HUIV26

Mab HUIV26 was generated by the immunological technique termed subtractive immunization (S.I.) as outlined in Example 1. As shown in FIG. 11, HUIV26 was shown to specifically recognize denatured collagen type-IV but does not bind to native triple helical collagen type-I or type-IV. In addition, Mab HUIV26 does not bind to other matrix components such as Laminin, Fibronectin, Vitronectin or fibrinogen, thus demonstrating its specificity to a cryptic epitope within collagen type-IV.

Figure 12:
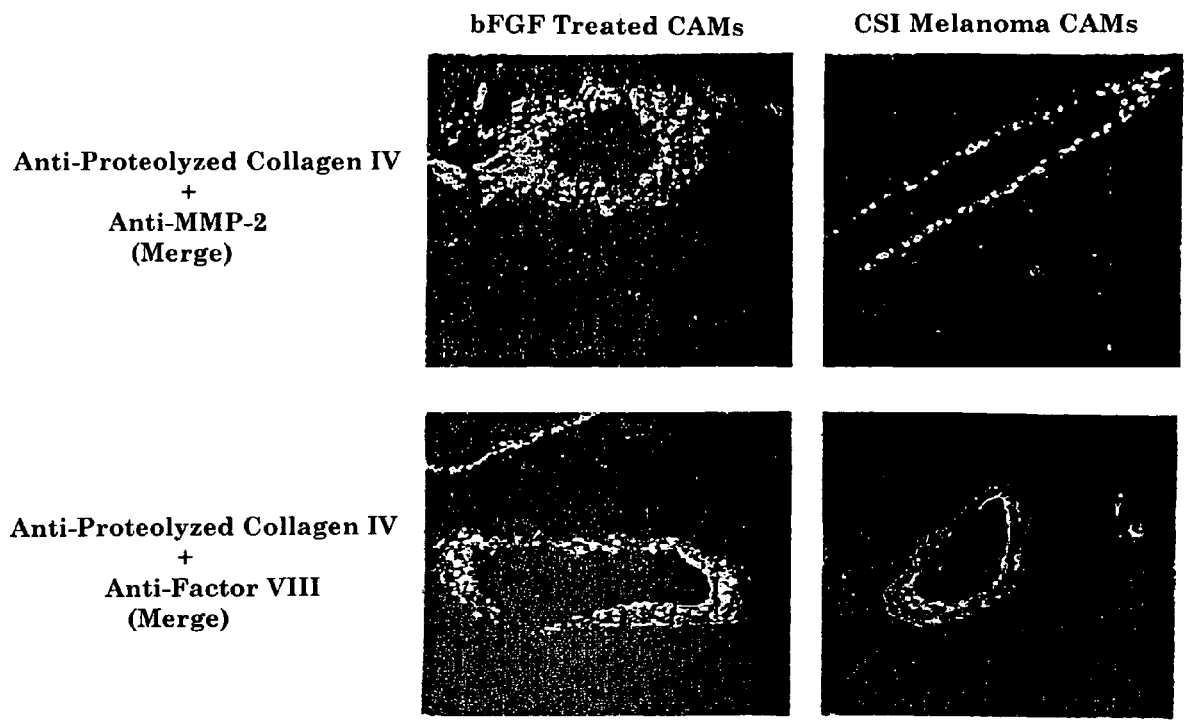
FIG. 12 demonstrates that Mab HUIV26 identifies denatured collagen-IV Surrounding Angiogenic Blood Vessels Within the Chick Chorioallantoic Membrane (CAM). The generation and localization of denatured collagen-IV in vivo was studied by indirect immunofluoresence on frozen tissue sections of CAM tissue from both bFGF induced and tumor induced angiogenesis. Frozen CAM tissue sections were fixed in acetone, blocked with 1% BSA and co-stained with Mab HUIV26 and polyclonal antibodies directed to either the collagen-IV degrading enzyme MMP-2 or Factor VIII. Antibody binding was detected by incubation with goat-anti-mouse FITC conjugated and goat anti-rabbit rhodamine conjugated secondary antibody. Top panels show co-localization of denatured collagen-IV and MMP-2 surrounding angiogenic blood vessels. Bottom Panels show co-localization of denatured collagen-IV and factor VIII surrounding angiogenic blood vessels. Left panels indicate CAM tissue stimulated with bFGF. Right panels indicate CAM tissue with CS1 melanoma tumors growing within it. Red color in the top panels indicate MMP-2 expression and in the bottom panels it indicates factor VIII expression. Green color in both the top and bottom panels indicate denatured collagen-IV expression. Yellow indicates co-localization.

As shown in FIG. 11B, the cryptic site(s) in type-IV collagen recognized by Mab HUIV26 are revealed after exposure to HUVEC conditioned media. The amount of reactivity with Mab HUIV26 increased over the 24 hour period examined. This indicates that these endothelial cells secrete a protease capable of unmasking the cryptic site in type-IV collagen recognized by Mab HUIV26. The protease produced by HUVEC that unmasks the cryptic site in type-IV collagen is inhibited by the chelator, EDTA (FIG. 11B). This suggests that a metalloprotease is responsible for initiating the unmasking of the cryptic site(s) in type-IV collagen. As shown in FIG. 12, the metalloprotease, MMP-2, colocalizes with the cryptic site(s) in type-IV collagen reacting with Man HUIV26 in angiogenic sites in CAM tissue. The serine protease inhibitor, aprotinin, had little effect on unmasking of cryptic site(s) in type-IV collagen after one hour of incubation with HUVEC conditioned media (FIG. 11B). At the 6 and 24 hour time points, the presence of aprotinin blocked 40 and 70 percent respectively of the reactivity observed in the absence of the protease inhibitor. This suggests that at the later time points (6 and 24 hour), serine proteases contribute to the unmasking of cryptic site(s) in type-IV collagen.

Example 9

Detection of Angiogenesis and Tumors with HUIV26

This example shows that an antagonist can be used to detect angiogenic processes within tissues.

As shown in FIG. 12, indirect immunofluoresence analysis of chick CAM tissue indicates the generation and localization of denatured collagen type-IV associated with either βFGF or tumor induced angiogenic blood vessels in vivo. Importantly, little if any evidence of denatured collagen-IV was detected in normal CAM tissues in the absence of bFGF or tumors, suggesting that denatured collagen-IV may be a specific marker of angiogenic blood vessels in vivo.

Indirect immunofluoresence analysis, shown in FIG. 13, of human melanoma tumor biopsies demonstrates the generation and localization of denatured collagen-IV surrounding human tumor associated blood vessels in vivo. Importantly, little if any evidence of denatured collagen-IV was detected surrounding normal blood vessels in the absence of tumors, suggesting that denatured collagen may be a specific marker of angiogenic tumor associated blood vessels.

Example 10

Inhibition of Cell Migration and Adhesion by Mab HUIV26

This example shows that an Mab antagonist can inhibit endothelial cell migration and adhesion.

Figure 14:
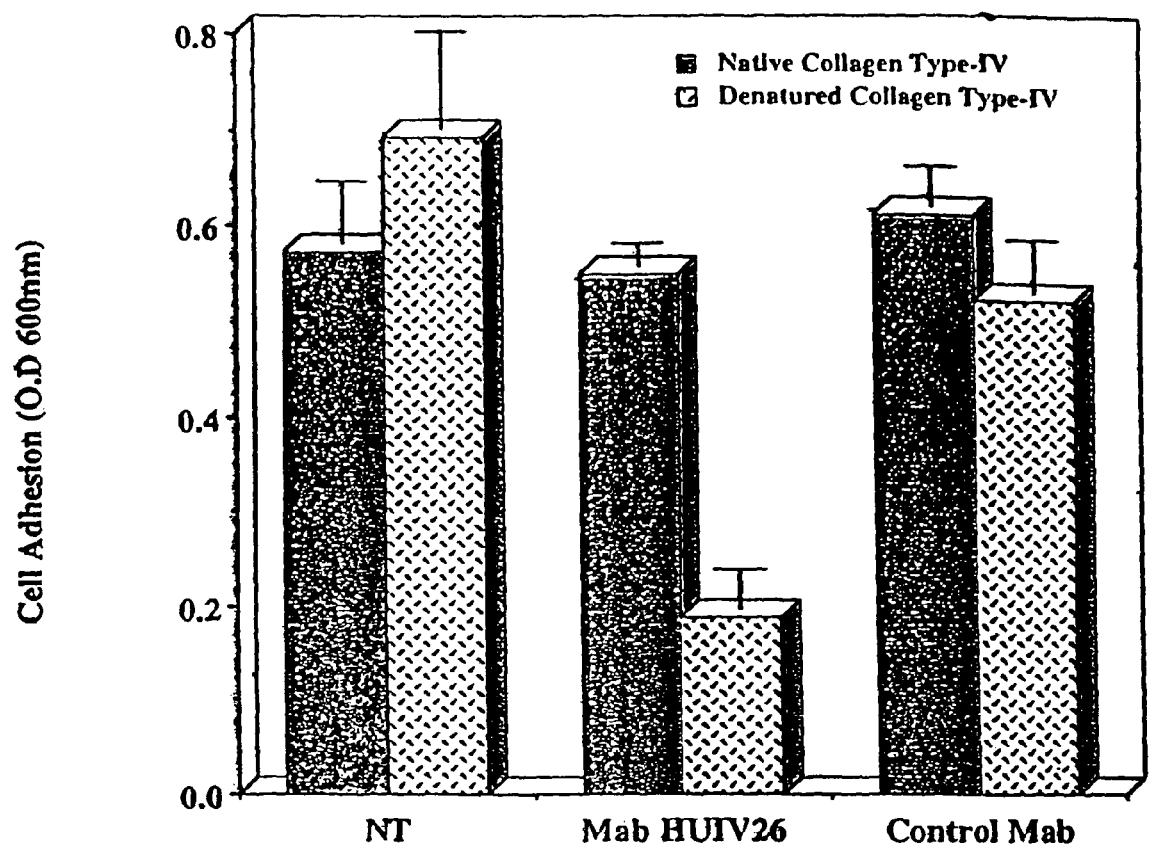
FIG. 14 demonstrates the effects of Mab HUIV26 on human endothelial cell adhesion. Microtiter plates (96 wells) were coated with either native or denatured collagen type-IV. Wells of the microtiter plate were next blocked with 1% BSA in PBS for 1 hour at 37° C. Human endothelial cells were then allowed to attach to the coated wells in the presence or absence of purified Mab HUIV26 or an isotype matched control antibody at a concentration of 100 ug/ml for 30 minutes. The non-attached cells were removed by washing and the attached cells were stained with crystal violet. Cells were next incubated with 10% acetic acid and cell adhesion was quantified by measuring the optical density (O.D) of eluted dye at 600 nm. Data Bars represent the mean O.D±standard deviation from triplicate wells.
Figure 15:
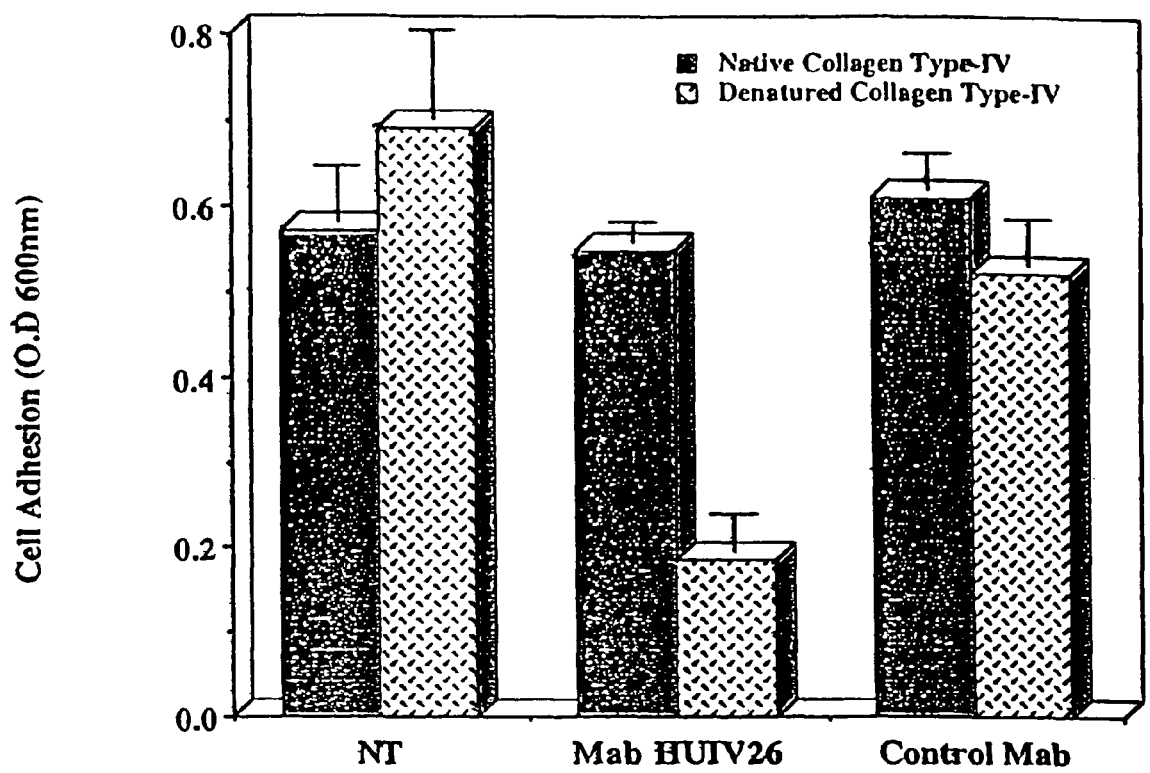
FIG. 15 shows the effects of Mab HUIV26 on human endothelial cell migration. Membranes from transwell migration chambers were coated with either native or denatured collagen type-IV. Human endothelial cells were then allowed so migrate to the underside of the coated membranes in the presence or absence of purified Mab HUIV26 or an isotype matched control antibody (100 ug/ml ) for a total of 6 hours. Cells remaining on the top side of the membrane were removed and the cells which had migrated to the underside of the membrane were stained with crystal violet. Membranes were next incubated with 10% acetic acid and cell migration was quantified by measuring the optical density (O.D) of eluted dye at 600 nm. Data Bars represent the mean O.D.±standard deviation from triplicate wells.

Mab HUIV26 showed the capacity to inhibit human endothelial cell adhesion to denatured collagen-IV by approximately 70% as compared to control antibody (FIG. 14). These findings suggest that Mab HUIV26 binds to a cryptic epitope within collagen type-IV that is at least partially involved in endothelial cell adhesion to denatured collagen-IV. Given the tissue distribution of collagen type-IV and the fact that cellular adhesive processes are thought to play a role in tumor growth and angiogenesis, this function blocking antibody may have an significant effect on angiogenesis and tumor growth in vivo.

Mab HUIV26 showed the capacity to inhibit human endothelial cell migration on denatured collagen-IV by approximately 70% as compared to control antibody or no treatment. These findings suggest that Mab HUIV26 binds to a cryptic epitope within collagen type-IV that plays a significant role in cellular migration on denatured collagen-IV. Given that cell migration is thought to play a important role in tumor metastasis and angiogenesis, and that denatured collagen was detected in association with angiogenic blood vessels, this function blocking antibody may have a significant impact on angiogenesis, tumor growth and metastasis in vivo.

Example 11

Inhibition of Angiogenesis by Systemic Administration of HUIV26

Figure 17:
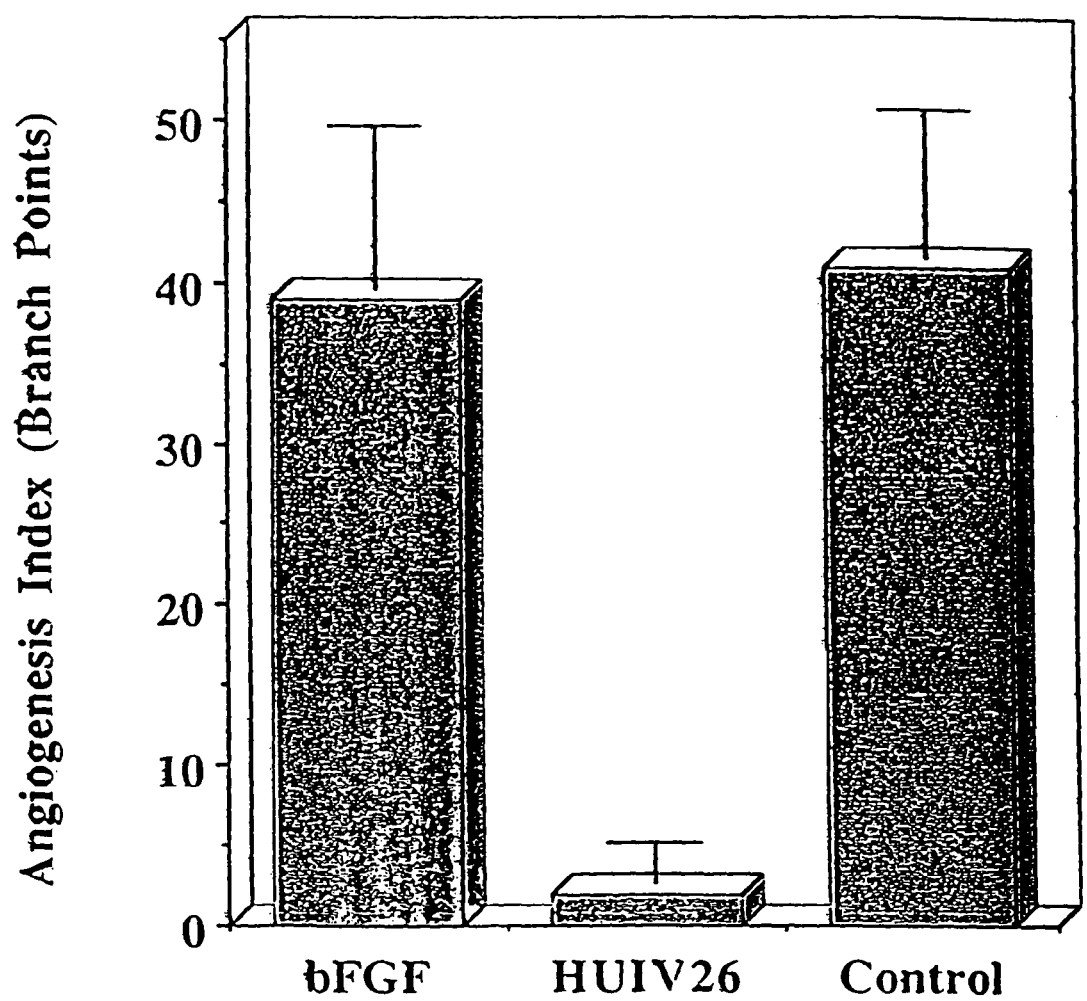
FIG. 17 shows quantification of the angiogenesis-experiments with Mab HUIV26. Data bars represent the mean±standard errors of 5 to 10 embryos per condition. Angiogenesis index is equal to the number of branch points from experimental treated embryos minus the number of branch points form CAMs in the absence of bFGF.
Figure 19:
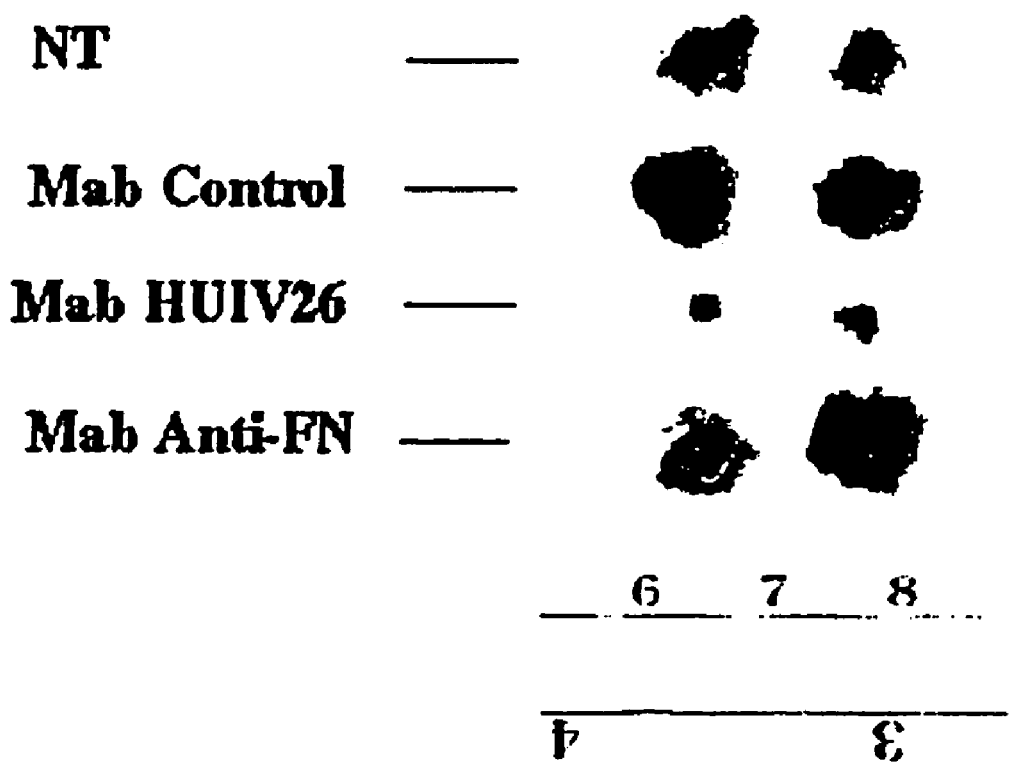
FIG. 19 shows size comparison of resected tumors. At the end of the 7 day incubation period the resulting tumors were resected and analyzed for overall size and wet weight. Photograph represents a comparison of the size of resected tumors from control or Mab HUIV26 treated embryos.
Figure 20:
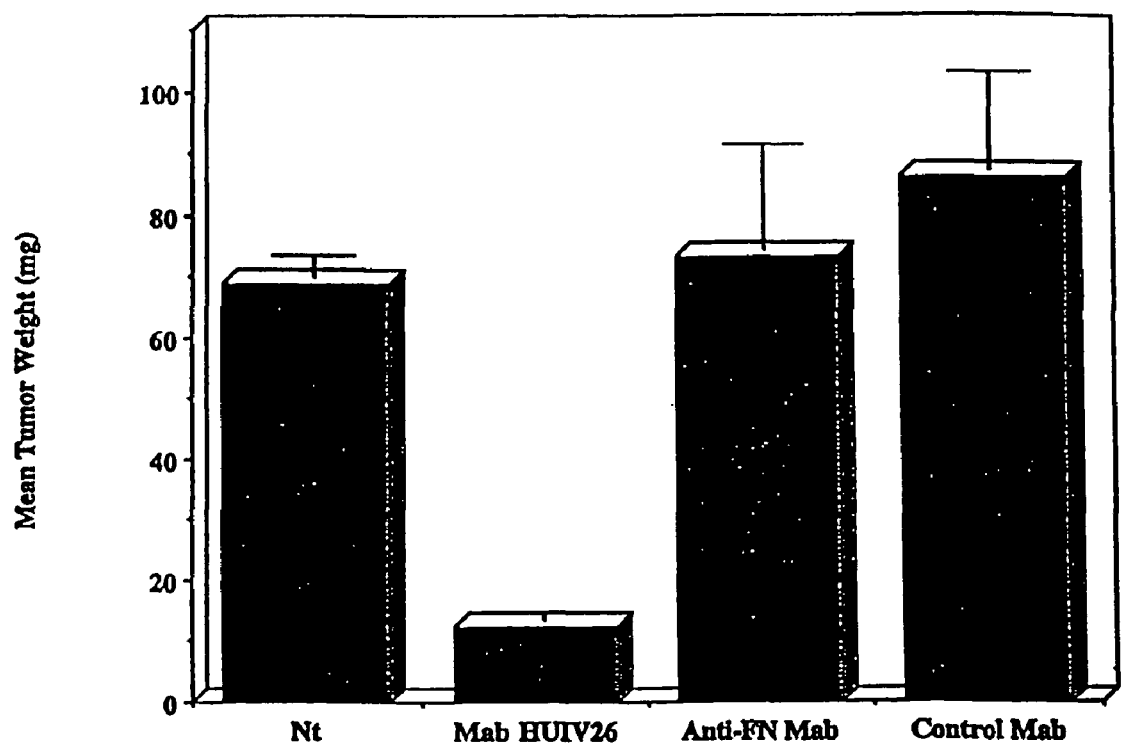
FIG. 20 shows quantification of the wet weight of the tumors. Data bars represent the mean±the standard errors of the tumor weight from 5 to 10 embryos per condition.
Figure 21:
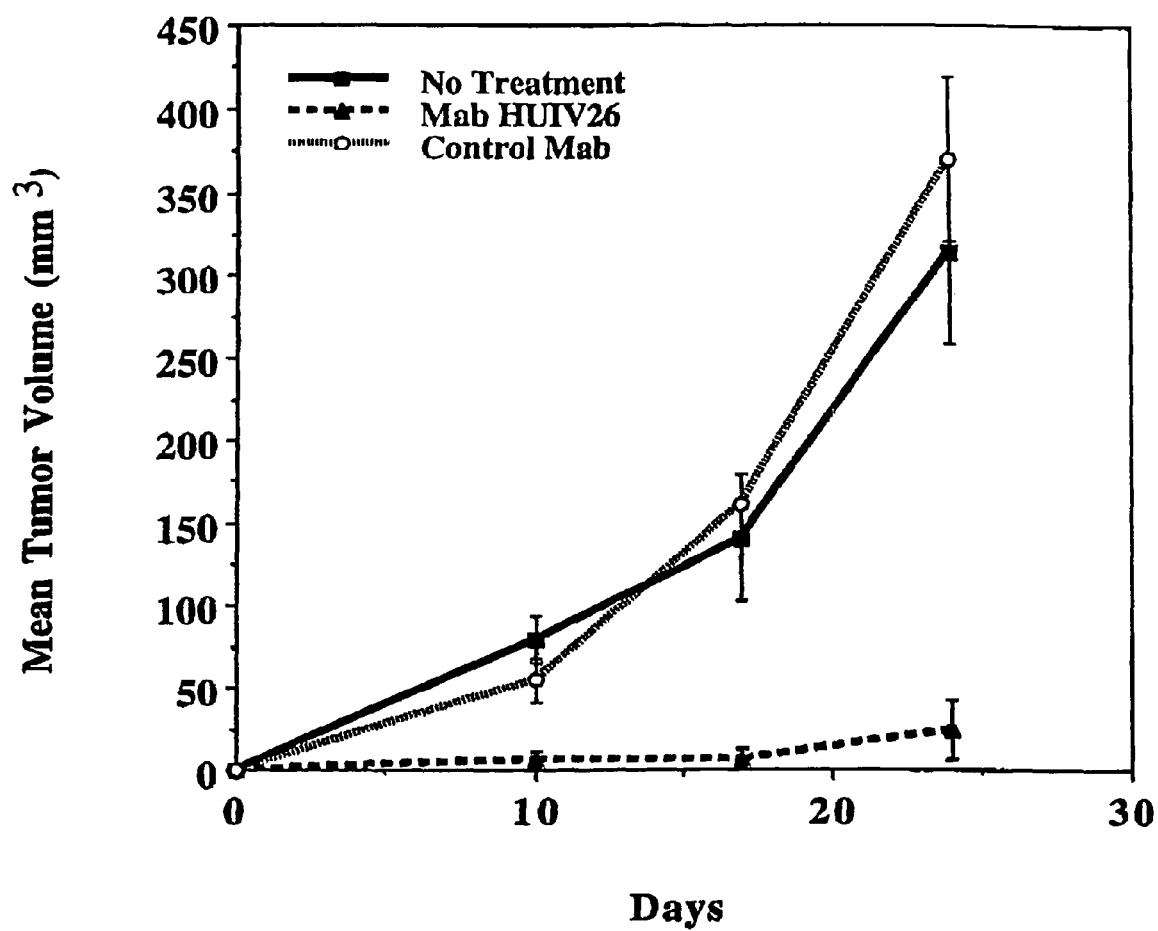
FIG. 21 shows the effects of Mab HUIV26 on tumor-growth assessed in a SCID mouse tumor model system. SCID mice were injected subcutaneously with $2 \times 10^6$ M21 human melanoma cells. Three days later a 24 day treatment was initiated with daily intraperitoneal injections of either 100 ug of either Mab HUIV26, an isotype matched control antibody, or without treatment. Tumor volume was monitored by caliper measurements and tumor volume was determined. Five mice were included in each group. The data represent the mean±standard errors of the tumor volumes for each experimental condition. Similar results were obtained in two independent experiments where five or ten mice were included in each experimental condition.

Systemic administration of Mab HUIV26 inhibited bFGF induced angiogenesis by approximately 90% as compared to controls, as shown in FIGS. 16 and 17. Importantly, no toxic side effects were noted in the embryos during the assay period. Moreover, few, if any, effects from this Mab were noted on normal quiescent blood vessels. It is possible that much lower concentration of Mab might be used and result in similar effects. These findings indicate that Mab HUIV26 is a potent anti-angiogenic reagent that may have significant clinical applications.

Example 12

Inhibition of Tumor Growth

Systemic administration of Mab HUIV26 inhibited melanoma tumor growth by approximately 80% as compared to controls (FIG. 18). Importantly, no toxic side effects were noted in the embryos during the assay period. Moreover, little if any effects from this Mab were noted on adjacent tissue. Additional experiments are now under way to determine an IC50 value since it is possible that much lower concentration of Mab might be used and result in similar effects. These findings indicate that Mab HUIV26 is a potent anti-tumor reagent that may have significant clinical applications.

Systemic administration of Mab HUIV26 inhibited melanoma tumor growth in SCID mice. After 24 days of treatment, Mab HUIV26 treated mice had an average tumor volume less than 5 percent that observed in mice treated with a control Mab or in mice not receiving treatment.

Example 13

Epitope Specificity of HUIV26

This example shows that HUIV26 is not binding to RGD sequences within denatured collagens.

As shown in FIG. 22, Mab HUIV26 fails to react with any of the immobilized RGD (arginine-glycine-aspartic acid) containing peptides found in type-IV collagen (Table 1). Six different soluble RGD containing peptides found in collagens failed to block the recognition of immobilized denatured type-IV collagen by Mab HUIV26 (FIG. 22). These data suggest that Mab HUIV26 does not recognize RGD sequences found in type-IV collagen.

TABLE 1

RGD Domains of Human Collagen Type-IV

| SEQ ID NO | Amino Acid Sequence | Position in Human Collagen Type-IV |
|---|---|---|
| 1 | C-PGS<u>RGD</u>TGP-C | α1 (IV) Chain (594-602) |
| 2 | C-SGP<u>RGD</u>PGL-C | α1 (IV) Chain (914-922) |
| 3 | C-KGS<u>RGD</u>PGT-C | α1 (IV) Chain (965-973) |
| 4 | C-KGA<u>RGD</u>PGF-C | α2 (IV) Chain (359-367) |
| 5 | C-PGP<u>RGD</u>AGV-C | α2 (IV) Chain (781-789) |
| 6 | C-PGD<u>RGD</u>PGD-C | α2 (IV) Chain (865-873) |
| 7 | C-SGD<u>RGD</u>AGF-C | α2 (IV) Chain (886-894) |
| 8 | C-KGS<u>RGD</u>PGP-C | α2 (IV) Chain (967-975) |
| 9 | C-IGS<u>RGD</u>KGA-C | α2 (IV) Chain (1066-1074) |
| 10 | C-PGE<u>RGD</u>PGE-C | α2 (IV) Chain (1245-1253) |
| 11 | C-PGF<u>RGD</u>EGP-C | α2 (IV) Chain (1489-1497) |

Example 14

Monoclonal Antibody XL313

Mab XL313 was generated by immunization with a synthetic peptide, the sequence of which was derived from human collagen type-I. The sequence was chosen because it is buried within the three dimensional structure of collagen type-I. The sequence of the 11 amino acid residue synthetic peptide used was:

SEQ ID NO 12:
CysGlnGlyProArgGlyAspLysGlyGluCys

The KGE (LysGlyGlu) sequence was found to be very important for XL313 recognition. Mab XL313 specifically binds to peptides of SEQ ID NO 1, but has substantially decreased binding affinity for peptides in which the KGE sequence has been mutated:

SEQ ID NO 13:
CysGlnGlyProArgGlyAspAlaAlaAlaCys

Figure 27:
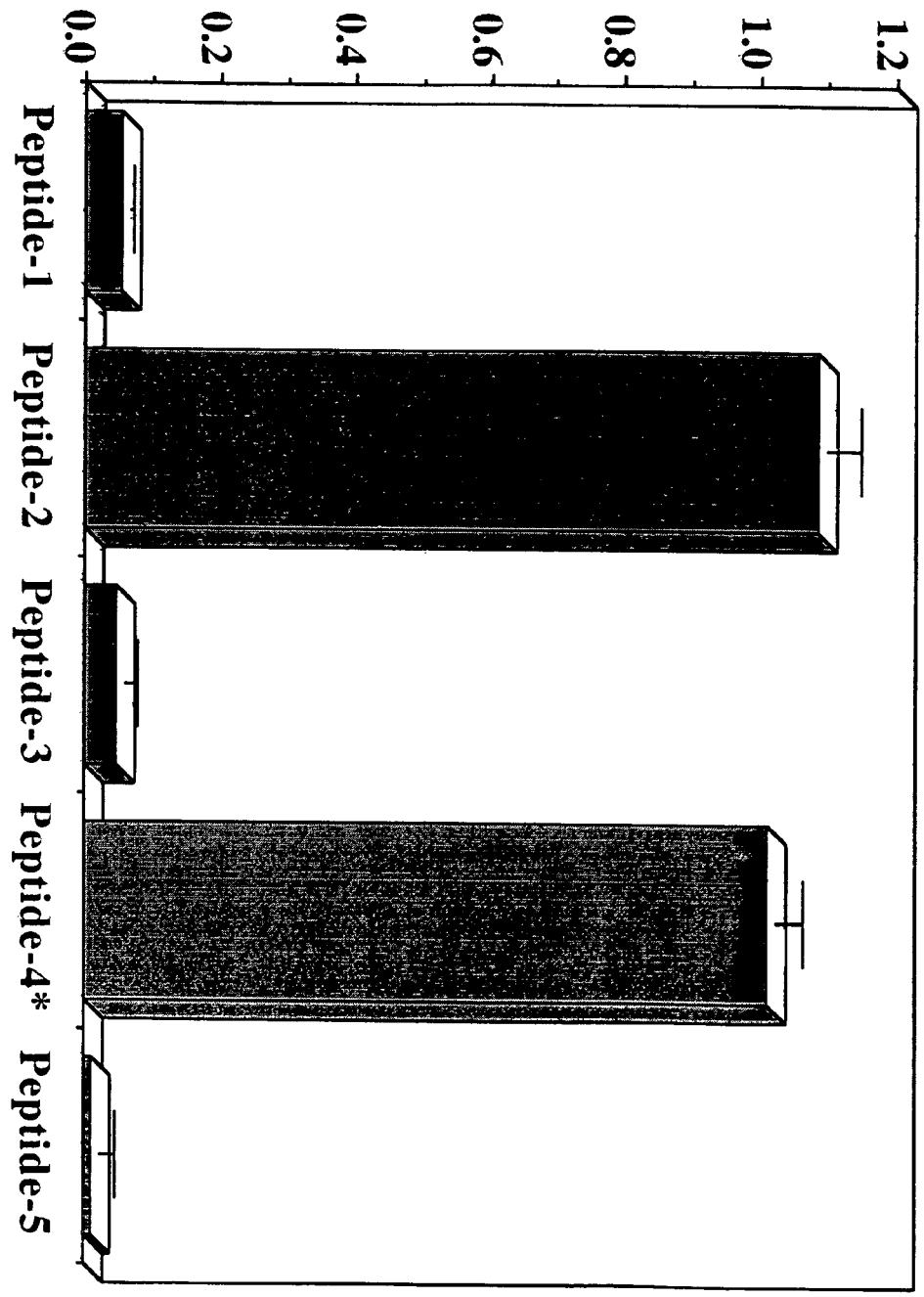
FIG. 27 demonstrates the generation of Mabs reactive with cryptic domains of collagen type-I. Cryptic domains of collagen type-I were used to generate Mabs. One of these Mabs termed XL313 was used for further study. Human collagen-I peptides were immobilized on microtiter wells and purified Mab XL313 binding was assessed. As shown below, Mab XL313 specifically recognized human collagen peptide-2. In addition Mab XL313 also recognized collagen peptide-4, however, collagen peptide-4 is not present in mature collagen-I. XL313 did not react with other similar collagen type-I peptides.
Figure 28:
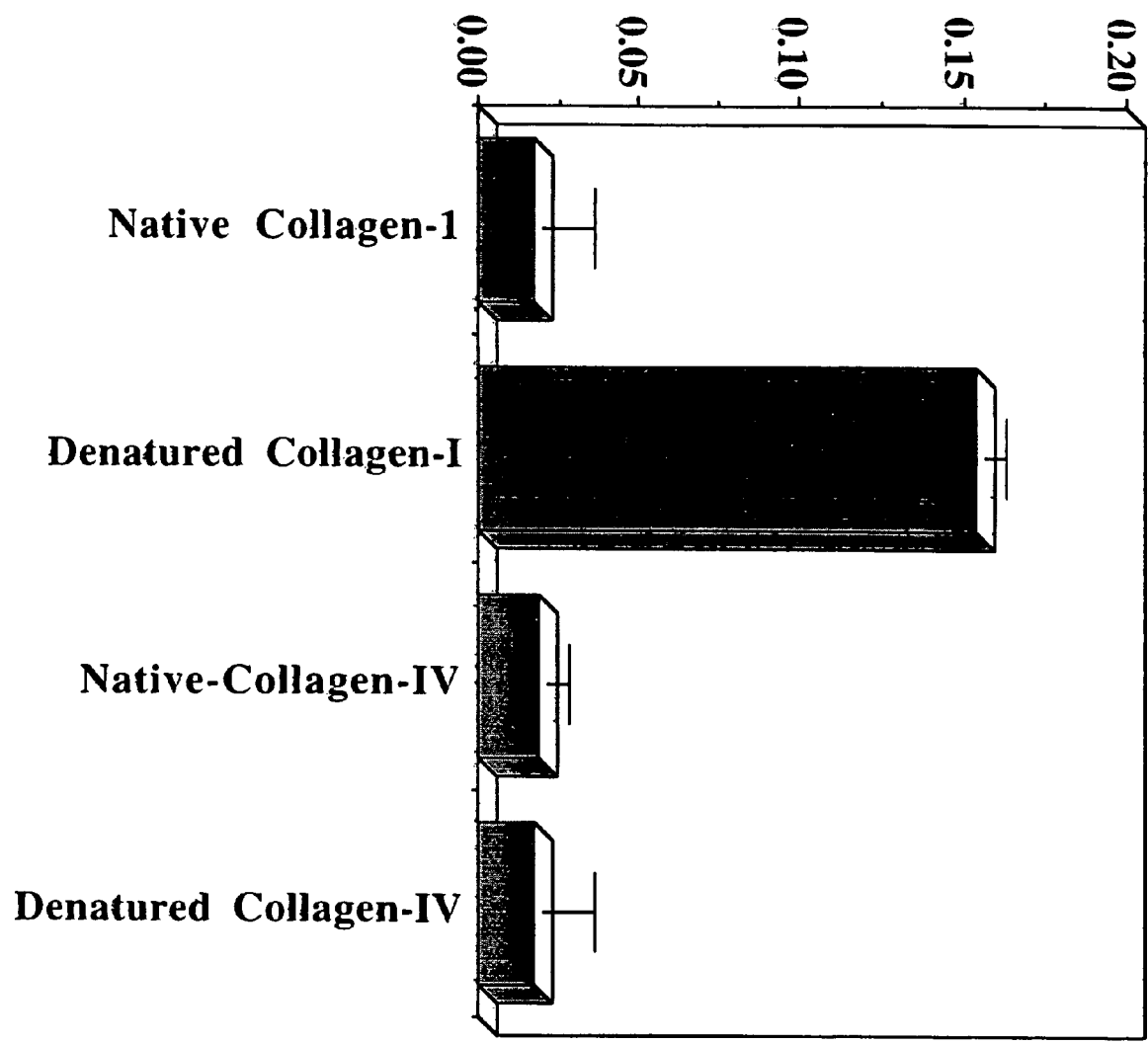
FIG. 28 shows that Mab XL313 specifically recognizes denatured human collagen type-I. Microtiter wells were coated with either native or denatured human collagen type-I or type-IV. The capacity of Mab XL313 to bind to native or denatured human collagen type-I and denatured collagen type-IV was assessed by solid phase ELISA. Mab XL313 specifically recognized denatured human collagen type-I but not native collagen type-I. In addition, Mab XL313 failed to bind to native or denatured human collagen type-IV.

Mab termed XL313 is a highly specific antibody that reacts with proteolyed/denatured collagen type-I. Importantly, XL313 does not react with the native triple helical form of collagen type-I. As shown in FIG. 27, Mab XL313 recognizes a cryptic domain of human collagen-I, but not other similar peptides. These data suggest that Mab XL313 may be a useful reagent to assess the role of the cryptic collagen domain defined by human collagen peptide-2 in angiogenesis and tumor growth. As shown in FIG. 28, Mab XL313 specifically recognizes a cryptic domain within human collagen-I that is not exposed within the mature triple helical conformation. Moreover, this cryptic domain appears to be specific to collagen-I as XL313 does not cross react with native triple helical collagen-IV.

Example 15

Mab XL313 Inhibits Cell Adhesion and Migration

As shown in FIG. 23, at the end of 5 hours, incubation HUVECs allowed to attach to native collagen-I formed a confluent monolayer. In contrast, HUVECs attached to denatured collagen began to migrate and morphologically reorganized to form cord-like structures. These data suggest that cryptic domains hidden within the three dimensional structure of human collagen-I, that are not assessable in its native triple helical state may play a role in endothelial morphogenesis and cord formation.

Example 16

Denatured Collagen Suppresses Apoptosis

Figure 24:
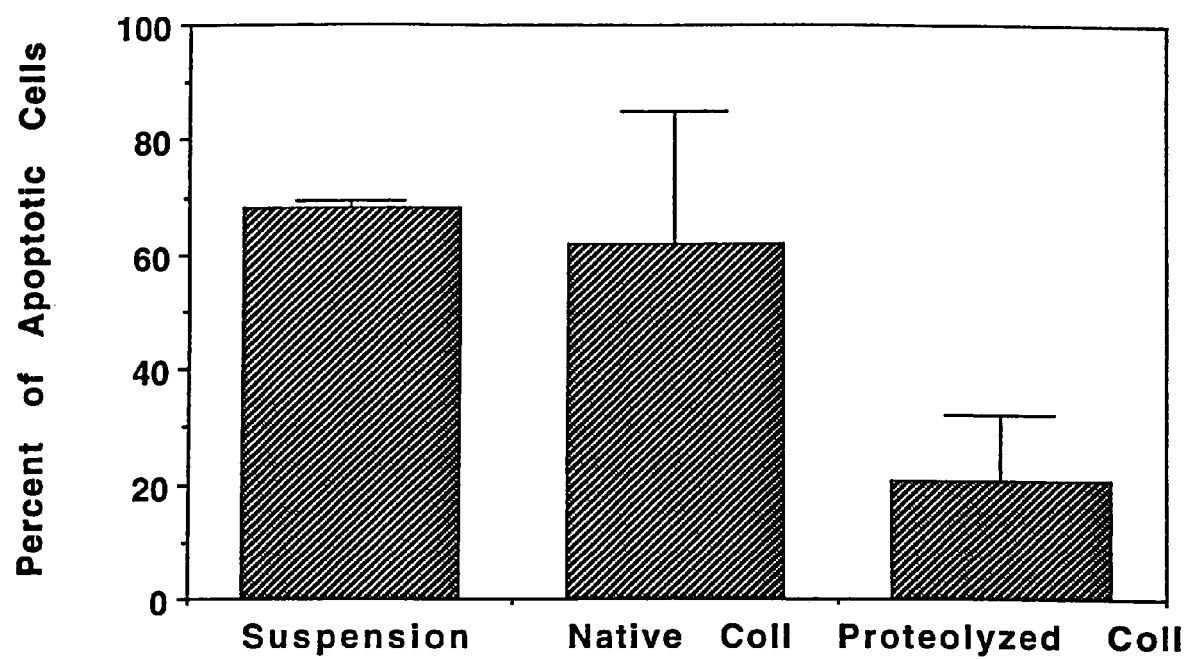
FIG. 24 shows analysis of endothelial cell survival on collagen type-I. Microtiter wells were coated with either native or proteolyzed/denatured human collagen type-I. HUVECs were next allowed to attach to the wells in the absence of added growth factors or serum for 5 hours. At the end of the 5 hour incubation, attached cells were removed, fixed and stained for apoptosis with ApopTag kit and analyzed by flow cytometry. Data indicated the mean±standard deviations of the percentage of human endothelial cells that were beginning to undergo apoptosis. Data were derived from triplicate wells.

As shown in FIG. 24, Human endothelial cell interactions with proteolyzed collagen suppresses apoptosis as compared to either native collagen-I or endothelial cells kept in suspension. These data suggest that cryptic domains hidden within the three dimensional structure of human collagen-I, that are not accessable in its native triple helical state may play a role in endothelial cell survival.

Example 17

The Epitope Recognized by XL313

Figure 25:
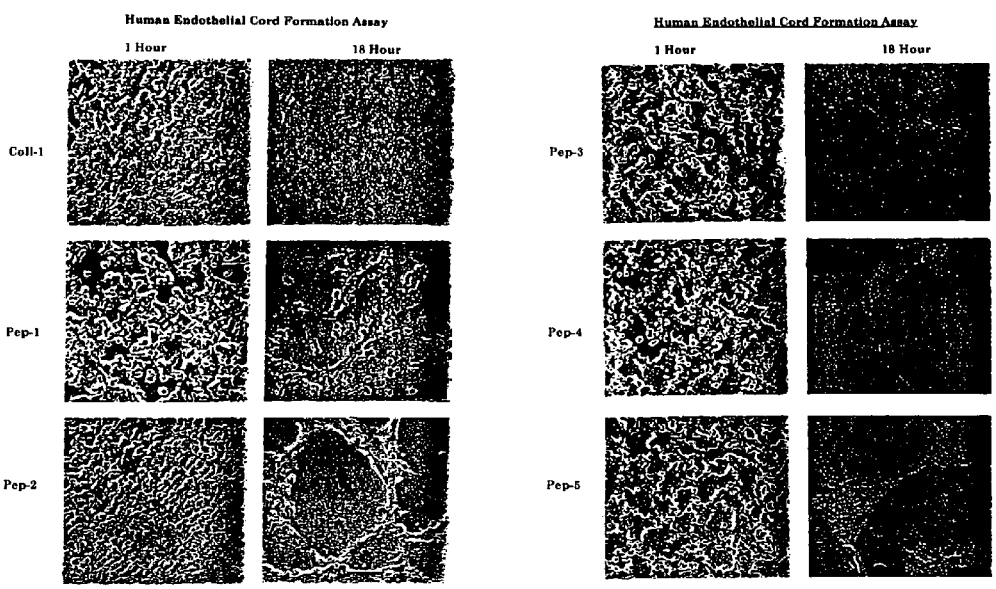
FIG. 25 shows effects of cryptic collagen type-I domains on endothelial cord formation. Analysis of human collagen-I amino acid sequence and three dimensional structure revealed potential cryptic domains that would be inaccessible within mature triple helical collagen-I. Synthetic peptides were generated corresponding to 5 of these potential cryptic domains of human collagen-I. These cryptic domains were immobilized on microtiter wells and endothelial cord formation assays were conducted as described above. As shown, all 5 collagen peptides supported endothelial cell adhesion by 1 hour following plating. However, human collagen peptide-2 was shown to facilitate endothelial cord formation and potentiate endothelial cell survival after 18 hours, while the other peptides showed little if any activity at the 18 hour time point.

As shown in FIG. 25, human collagen cryptic peptide-2 appears to support endothelial cell survival and cord formation, while similar cryptic peptides present within human collagen-I show little if any effect. These data suggest that the cryptic region of collagen-I defined by peptide-2 may play an important role in angiogenesis and tumor growth in vivo.

Example 18

Role of Integrins

As shown in FIG. 26, integrin $\alpha v\beta 3$ appears to play a major role in mediating cellular interactions with all the cryptic peptide domains of collagen-I tested. Interestingly, peptide-2 was also dependent on $\beta 1$ integrin interaction. These data suggest that peptide-2 supports cellular interactions by 2 distinct integrins.

Example 19

Mab XL313 Inhibits Angiogenesis and Tumor Growth

Figure 30:
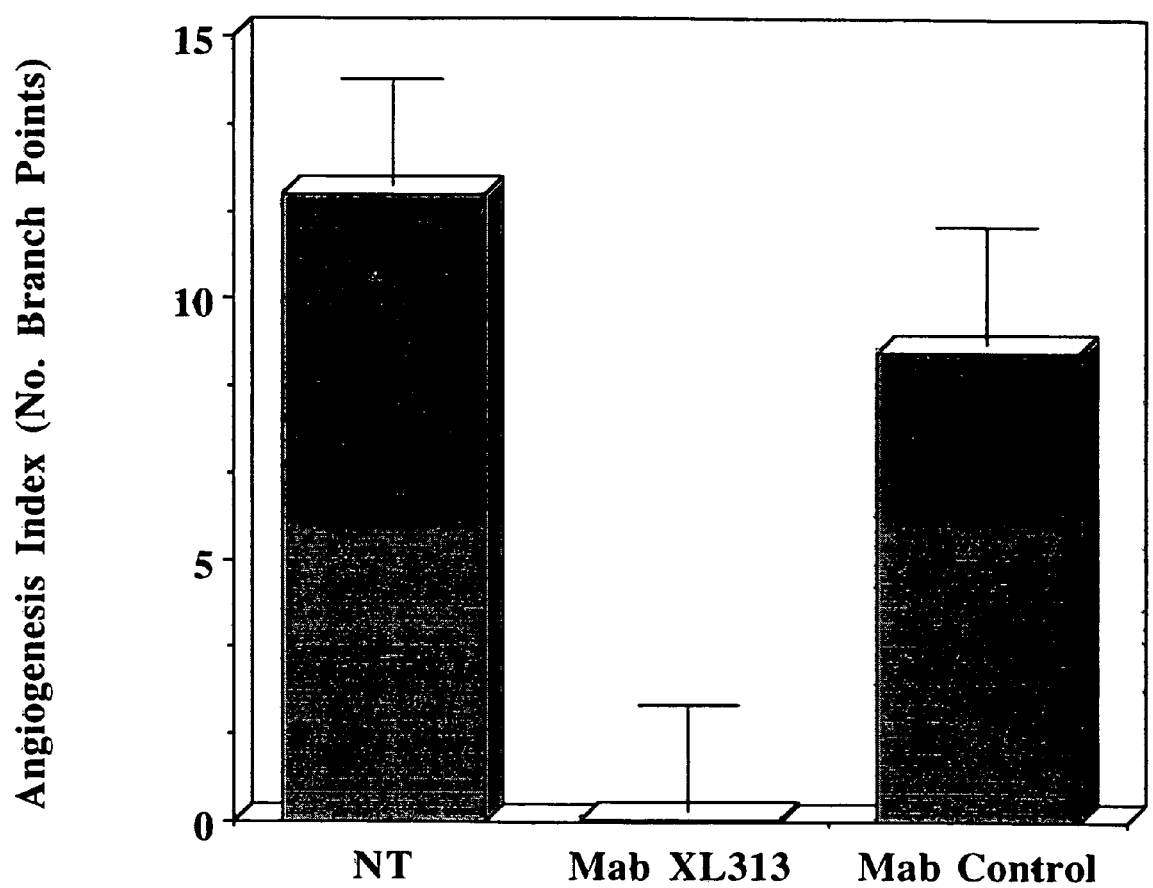
FIG. 30 shows quantification of the angiogenesis experiments of FIG. 29. Data bars represent the mean±standard errors of 5 to 10 embryos per condition.

As shown in FIGS. 29 and 30, Systemic administration of Mab XL313 inhibited angiogenesis in the Chick CAM model by over 95% as compared to controls. These data suggest that the cryptic domain of collagen-I defined by Mab XL313 plays an important role in angiogenesis.

Figure 31:
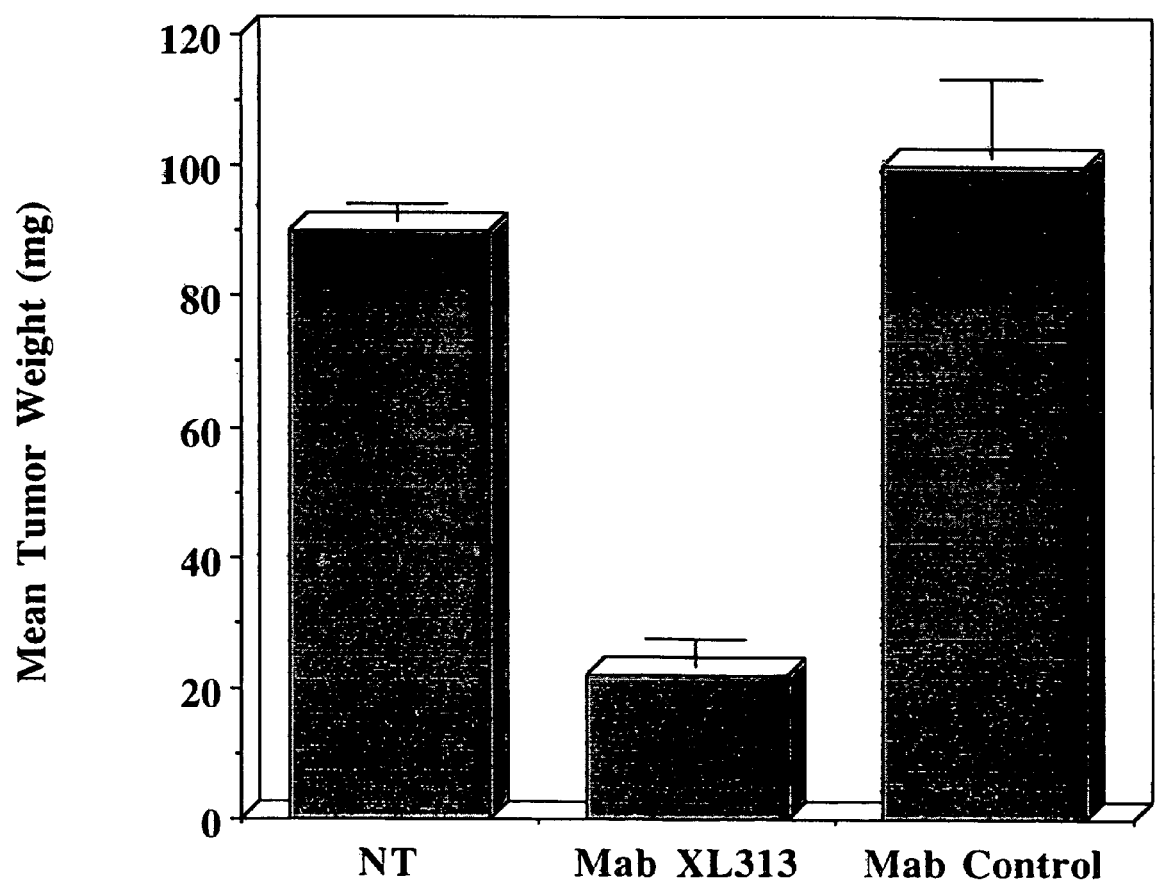
FIG. 31 shows the effects of systemic administration of Mab XL313 on human fibrosarcoma tumor growth. HT1080 human fibrosarcoma cells ($5 \times 10^6$) were inoculated on the CAMs of 10 day old chick embryos. Twenty-four hours later the embryos received a single intravenous injection of purified Mab XL313 at concentrations of 50 μg per embryo. After 7 days, tumors re resected and wet weights determined. Quantification of tumors weight. Data bars represent the mean±the standard errors from 5 to 10 embryos per condition.

As shown in FIG. 31, Mab XL313 potentially inhibits HT1080 fibrosarcoma tumor growth in vivo. These findings indicate that the cryptic domain defined by Mab XL313 may play a significant role in regulating tumor growth in vivo.

Example 20

Proteolysis of Collagen is Important for Tumor Growth

Figure 32:
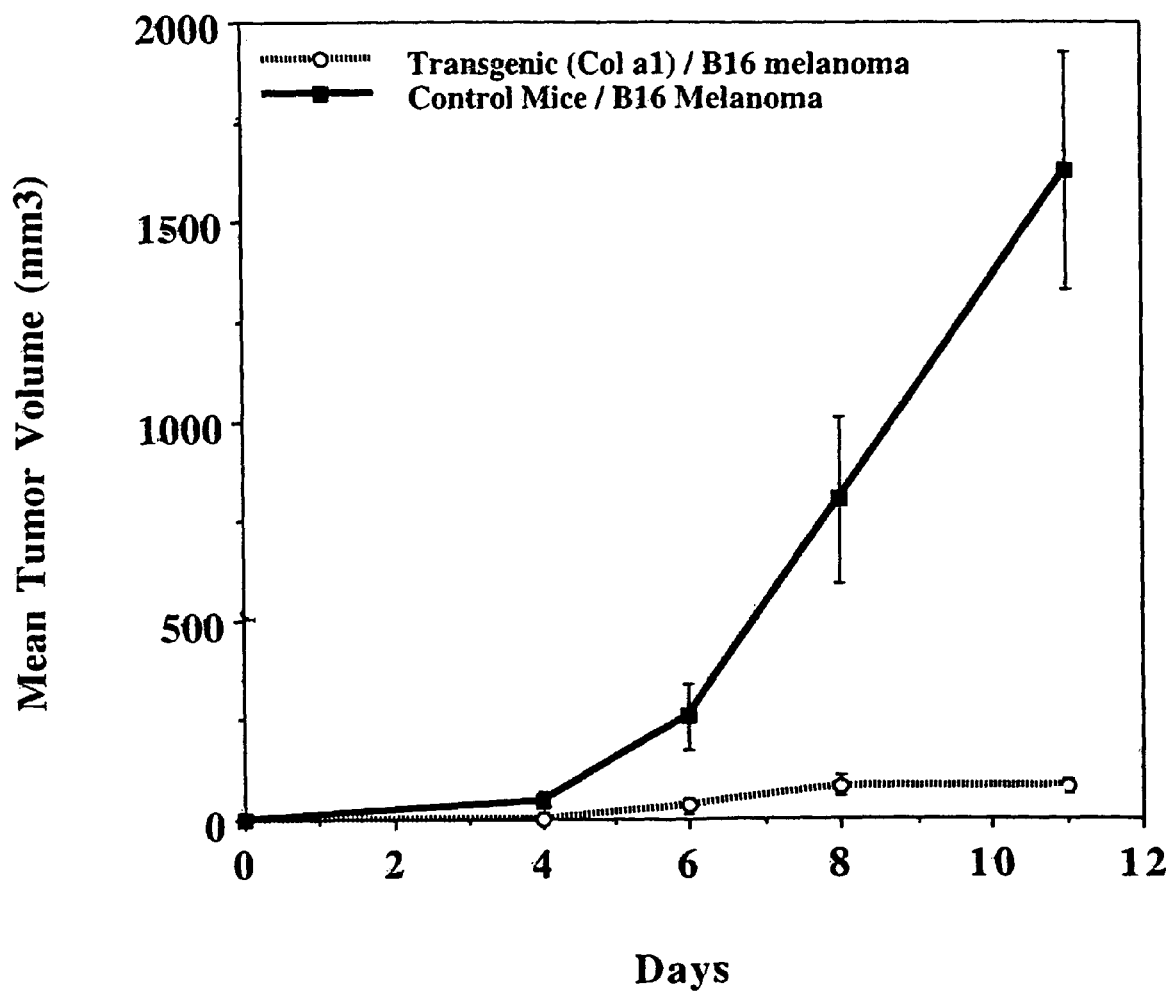
FIG. 32 shows that mutation in the MMP cleavage site of collagen-I inhibits melanoma tumor growth in vivo. Transgenic mice that harbor a mutation in the MMP cleavage site within collagen-I were used to determine if proteolysis of collagen type-I may play a role in tumor growth and angiogenesis. Col a1 transgenic mice have a mutation which inhibits binding of MMPs and cleavage of collagen type-I. Col a1 B6 transgenic mice or wild type control B6 mice were injected subcutaneously with B16 transgenic melanoma tumor cells. Tumors were allowed to develop for 11 days and tumor size was monitored with calipers. As show below, B16 melanoma cells formed large proliferating tumors within mice that can readily proteolyze collagen type-I. In contrast, B16 melanoma cells exhibited little if any capacity to form tumors in the B6 Col a1 transgenic mice in which collagen type-I proteolysis is inhibited. Data represent the mean±standard errors of the tumor volumes from 5 mice per condition.

As shown in FIG. 32, transgenic mice in which a mutation was introduced within the MMP cleavage site of collagen-I molecule was used in this experiment since these mice have impaired ability to proteolyze their collagen-I. Importantly, B16 melanoma cells exhibited little, if any, ability to form tumors in mice that exhibit impaired collagen-I proteolysis as compared to wild-type control mice. These data suggest that proteolysis of collagen-I plays an important role in tumor growth in vivo.

As was demonstrated with B16 melanoma cells, Lewis lung carcinoma cells also exhibited little, if any, capacity to form tumors when injected in Col a1 B6 transgenic mice which have impaired ability to proteolyze their collagen-I, while Lewis lung carcinoma cells form large rapidly growing tumors in control B6 mice (FIG. 33). Importantly, Mab XL313, specifically directed to a cryptic domain within collagen-I which is only exposed following proteolysis, inhibited Lewis lung carcinoma tumor growth in wild-type B6 mice by approximately 80%. The findings suggest that proteolytic exposure of the cryptic domain of collagen-I in vivo may play an important role in tumor growth. Moreover, these data suggest that Mab XL313 is a specific inhibitor of angiogenesis and tumor growth in vivo.

All of the following publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

Deposit Information

A deposit of the monoclonal antibodies HU177 and XL313 disclosed above and recited in the appended claims has been made with the American Type Culture Collection (ATCC). 10801 University Boulevard, Manassas, VA 20110. The date of deposit of monoclonal antibodies HU177 and XL313 was Feb. 2, 2005. The date of deposit of monoclonal antibody HUIV26 with the ATCC was Feb. 9, 2005. The ATCC accession numbers have been assigned as follows:

HU177 has been assigned PTA-6551;
XL313 has been assigned PTA-6552; and
HUIV26 has been assigned accession number PTA-6563.

The deposits will be maintained in the depository for a period of 30 years, 5 years after the most recent request for a sample, or for the effective life of the patent, whichever is longer, and will be replaced as necessary during that period.

---

What is claimed is:

1. A method for inhibiting angiogenesis in a tissue comprising administering to a patient in need of the inhibition of angiogenesis, a therapeutically effective amount of an antagonist that specifically binds to a denatured collagen or collagens but binds to the native triple helical form of each of said collagens with substantially reduced affinity, wherein said antagonist inhibits angiogenesis, and wherein the antagonist is an antibody having the binding specificity of monoclonal antibody HU177, HUIV26, or XL313.

2. The method of claim 1 wherein said antagonist is administered in conjunction with chemotherapy or radiation.

3. The method of claim 1 wherein the tissue is inflamed and angiogenesis is occurring.

4. The method of claim 3 wherein the tissue is present in a mammal.

5. The method of claim 3 wherein the tissue is arthritic, ocular, retinal, a hemangioma, an angiofibroma, a Kaposi's sarcoma, or a solid tumor of the lung, pancreas, breast, colon, larynx, ovary or skin.

6. A method for inhibiting tumor growth or metastasis comprising administering to a patient in need of the inhibition of angiogenesis, a therapeutically effective amount of an antagonist that specifically binds to a denatured collagen or collagens but binds to the native triple helical form of each of said collagens with substantially reduced affinity, wherein said antagonist inhibits angiogenesis, and wherein the antagonist is an antibody having the binding specificity of monoclonal antibody HU177, HUIV26, or XL313.

7. The method of claim 6 wherein said antagonist is administered intravenously, transdermally, intrasynovially, intramuscularly, intratumorally, intraocularly, intranasally, topically or orally.

8. The method of claim 6 wherein said antagonist is administered in conjunction with chemotherapy or radiation.

9. The method of claim 6 wherein the tumor or metastasis is a melanoma, carcinoma, sarcoma, fibrosarcoma, glioma, astrocytoma, angiofibroma, a solid tumor of the lung, pancreas, breast, colon, larynx, ovary or skin, or Kaposi's sarcoma.

10. A method of inhibiting psoriasis, macular degeneration, or restenosis in a tissue comprising administering to a patient in need of the inhibition of angiogenesis, a therapeutically effective amount of an antagonist that specifically binds to a denatured collagen or collagens but binds to the native triple helical form of each said collagens with substantially reduced affinity, wherein said antagonist inhibits angiogenesis, and wherein the antagonist is an antibody having the binding specificity of monoclonal antibody HU177, HUIV26, or XL313.

11. The method of claim 10 wherein said antagonist is administered intravenously, transdermally, intrasynovially, intramuscularly, intratumorally, intraocularly, intranasally, topically or orally.

12. The method of claim 10 wherein said antagonist is administered in conjunction with chemotherapy or radiation.

* * * * *